United States Patent
Tomich et al.

(10) Patent No.: US 7,745,570 B2
(45) Date of Patent: Jun. 29, 2010

(54) PH DEPENDENT ADHESIVE PEPTIDES

(75) Inventors: John Tomich, Manhattan, KS (US);
Takeo Iwamoto, Manhattan, KS (US);
Xinchun Shen, Chapel Hill, NC (US);
Xiuzhi Susan Sun, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 238 days.

(21) Appl. No.: 11/793,187

(22) PCT Filed: Dec. 16, 2005

(86) PCT No.: PCT/US2005/046137
§ 371 (c)(1),
(2), (4) Date: Nov. 26, 2007

(87) PCT Pub. No.: WO2006/127048
PCT Pub. Date: Nov. 30, 2006

(65) Prior Publication Data
US 2009/0105449 A1    Apr. 23, 2009

(51) Int. Cl.
*C07K 7/00* (2006.01)
*C07K 14/00* (2006.01)

(52) U.S. Cl. ...................................... 530/300
(58) Field of Classification Search ............ None
See application file for complete search history.

(56) References Cited

U.S. PATENT DOCUMENTS 5,368,712 A * 11/1994 Tomich et al. ......... 204/403.06

OTHER PUBLICATIONS

Terashita et al. "Two serine residues distinctly regulate the rescue function of Humanin, an inhibiting factor of Alzheimer's disease-related neurotoxicity: functional potentiation by isomerization and dimerization," Journal of Neurochemistry, 2003, 85, 1521-1538.*

* cited by examiner

*Primary Examiner*—Anish Gupta
*Assistant Examiner*—Christina Bradley
(74) *Attorney, Agent, or Firm*—Medlen & Carroll, LLP

(57) ABSTRACT

A novel peptide adhesive motif is described that requires no receptor or cross-links to achieve maximal adhesive strength. Several peptides with different degrees of adhesive strength have been designed and synthesized using solid phase chemistries. All peptides contain a common hydrophobic core sequence flanked by positively or negatively charged amino acids sequences.

6 Claims, 17 Drawing Sheets

| Peptides | Sequence | MW | pI | ΔG$_{ave}$ (Kcal/mol) | |
|---|---|---|---|---|---|
| | | | | pH 7.0 | pH 12.0 |
| K$_3$h$_{5n}$K$_3$ | KKK-IGSII-KKK | 1269.7 | 10.70 | 0.90 | -0.46 |
| K$_3$h$_{5c}$K$_3$ | KKK-FLIVI-KKK | 1371.8 | 10.70 | 0.68 | -0.69 |
| K$_2$h$_{5n}$K$_2$ | KK-IGSII-KK | 1013.3 | 10.48 | 0.70 | -0.41 |
| K$_2$h$_{5c}$K$_2$ | KK-FLIVI-KK | 1115.5 | 10.48 | 0.42 | -0.69 |
| K$_3$h$_7$K$_3$ | KKK-FLIVIGS-KKK | 1516.0 | 10.70 | 0.68 | -0.47 |
| K$_3$h$_9$K$_3$ | KKK-FLIVIGSII-KKK | 1742.3 | 10.70 | 0.36 | -0.51 |
| K$_3$h$_{11}$K$_3$ | KKK-VFFLIVIGSII-KKK | 1988.6 | 10.70 | 0.36 | -0.52 |
| K$_3$h$_{12}$K$_3$ | KKK-FLIVIGSIIVIL-KKK | 2067.8 | 10.70 | 0.32 | -0.51 |
| KAE$_{16}$ | KAKAKAKAEAEAEAEA | 1614.8 | 6.29 | 1.02 | 0.40 |

FIG 13

PH DEPENDENT ADHESIVE PEPTIDES

STATEMENT OF GOVERNMENT SUPPORT

Partial support for these studies was provided by US Department of Energy (Grant #DE5 FC07-01ID14217). The US Government, therefore, has certain rights in this invention.

FIELD OF INVENTION

This invention relates to peptide synthesis of adhesive peptides based on a mixture of hydrophobic and β-sheet stacking interactions. In one embodiment, the peptide adhesive comprises a hydrophobic segment promoting rapid aggregation. In another embodiment, the peptide adhesive forms a network of interlocking strands.

BACKGROUND

Most commercial adhesives contain chemicals that are harmful to the environment. The development of safe bio-based adhesives holds the promise to attenuate these harmful effects. Strong protein (polypeptides) adhesives have been isolated from the phenol gland of mussels of the genus *Mytilus* (Papov et al., 1995; Waite, 1983; Yamamoto et al., 1983; 1990; 2000; Yu and Deming, 1998). Burzio and Waite (2000) showed that the adhesive strength of the principal mussel protein, mefp1, relies on DOPA-DOPA cross-links. The adhesive protein consists of tandem repeats of the consensus sequence AKPSYPPTYK (SEQ ID NO: 1) that have undergone posttranslational hydroxylation of the two tyrosines to DOPA.

These materials continue being studied since they can be prepared from a renewable resource, are biocompatible and biodegradable, and possess unique self-assembling properties.

Such protein adhesives have many potential applications, including tissue adhesives and bonding agents for implants and mucoadhesive drug delivery. On the other hand, abundant adhesive proteins are available from renewable resources and agricultural by-products such as soybean proteins. Developed in the 1920s, plant (soy) protein-based adhesives were used mainly in wood based products (e.g. particle board and plywood). Recently, modified soy protein-based adhesives have improved adhesive strength and water resistance (Hettiarachchy et al., 1995; Huang and Sun, 2000a,b; Sun and Bian, 1999; Kalapathy et al., 1995, 1996; Zhong et al., 2002). While the amino acid sequences of numerous adhesive proteins are known (Adachi et al., 2001; Nielsen, 1985; Staswick et al., 1981; 1984), the molecular interactions of protein binding on wood surfaces are poorly understood.

One molecular interaction is based upon the characteristic of the soy protein-based adhesives is the presence of long hydrophobic stretches of amino acids. Electrostatics do not appears to be important. The adhesive strength of wood composites bonded with isolated proteinaceous bioadhesives appears to be directly correlated to the number of the amine functional groups in the adhesive (Yamamoto et al., 1995). Also, peptides and protein-based polymers can be designed for a specific function using the biologically available native amino acids where the side chains are chemically modified with functional groups (Lee et al., 2001; van Hest and Tirrell, 2001; Yamamoto et al., 1995; Yamamoto et al., 1990).

What is needed is a rational design approach for making protein adhesives where the contributions of the different amino acid side chains, either singly or in groups, may be assayed for adhesive properties, secondary structure, and modes of action at the molecular level.

SUMMARY

This invention relates to solid-phase peptide synthesis of short adhesive peptides based on a mixture of hydrophobic and β-sheet stacking interactions. In one embodiment, the peptide adhesive comprises a hydrophobic segment promoting rapid aggregation. In another embodiment, the peptide adhesive forms a network of interlocking strands.

The present invention contemplates a composition comprising an adhesive protein comprising (or consisting of) a hydrophobic core attached to at least one tripeptide, wherein said hydrophobic core comprises (or consists of) FLIVIGSII (SEQ ID NO:2). In one embodiment, said tripeptide comprises (or consists of) lysine-lysine-lysine.

In one embodiment, said tripeptide comprises glutamic acid-glutamic acid-glutamic acid. In one embodiment, said tripeptide comprises diaminopropionic acid-diaminopropionic acid-diaminopropionic acid. In one embodiment, said adhesive protein further comprises tandem repeats of said hydrophobic core and said tripeptide. In one embodiment, said adhesive protein is selected from the group consisting of $E_3h_9E_3$, $K_3h_9E_3$, $E_3h_9K_3$, $K_3h_9K_3$, and $X_3h_9X_3$, wherein $h_9$=the hydrophobic core sequence FLIVIGSII (SEQ ID NO: 2); $K_3$=the tripeptide lysine-lysine-lysine, $E_3$=the tripeptide glutamic acid-glutamic acid-glutamic acid; and $X_3$=the tripeptide diaminopropionic acid-diaminopropionic acid-diaminopropionic acid. In one embodiment, said adhesive protein is selected from the group consisting of $(K_3h_9)_2K_3$ and $(K_3h_9)_3K_3$.

The present invention also contemplates varying the length of the aforementioned nine amino acid hydrophobic core, i.e. FLIVIGSII (SEQ ID NO:2), and subsequently measuring the adhesive properties of these varied length hydrophobic core proteins.

The present invention also contemplates embodiments wherein adhesive peptides are prepared as a "sol-gel solution". That is to say, a colloidal suspension which may transition from a liquid (sol) to a more solid material (gel). In a preferred embodiment, the "sol" is a suspension of aqueous adhesive peptide that is transitioned, by chemical treatment, into a gel. A gel refers to the state of matter between liquid and solid. As such, a "gel" has some of the properties of a liquid (i.e., the shape is resilient and deformable) and some of the properties of a solid (i.e., the shape is discrete enough to maintain three dimensions on a two dimensional surface.). In some embodiment a gel will be cast in a mold. In some embodiments these gels will be biocompatible insofar as they will not substantially disrupt the normal biological functions of other compositions to which they contact. It is also contemplated that the porosity of these gels may be varied according to known techniques.

The present invention also contemplates embodiments in which the aforementioned gels will function as a matrix comprising a plurality of pores dividing free space into partially enclosed interstices wherein said interstices are in fluidic communication. Such a matrix could act as a functional scaffold upon which cells could be seeded.

The present invention also contemplates embodiments, wherein the adhesive peptides described in the present invention gel in an organic solvent. This gel may be used to sequester organic solvents to facilitate disposal of the same. In other embodiments, said gel may be used to partition an aqueous phase from an organic phase.

In one embodiment, present invention contemplates a method, comprising: a) providing: i) a protein comprising FLIVIGSII (SEQ ID NO: 2) and at least one tripeptide; ii) a solution having an approximate pH 12; and b) contacting said protein with said solution under conditions that create an adhesive protein. In one embodiment, said adhesive protein comprises a beta-sheet conformation. In one embodiment, said β-sheet conformation comprises an anti-parallel orientation. In one embodiment, said adhesive protein comprises a hydrophobic core stabilized by Van der Waals interactions. In one embodiment, said adhesive protein comprises a shear strength in the range between 0.5-5.0 MPa. In one embodiment, said adhesive protein comprises a viscosity in the range between 0.1-350 mPa·sec.

In one embodiment, the adhesive peptides of the present invention self aggregate and interact with a wood surface having the following approximate adhesive strength, dry: 3.7-4.0 MPa; wet: 1.4 MPa.

In one embodiment the present invention contemplates a hydrophobic core protein comprising any five contiguous amino acid residues in the sequence: FLIVIGSIIVIL (SEQ ID NO: 15). In one embodiment the present invention contemplates a hydrophobic core protein comprising any six contiguous amino acid residues in the sequence: FLIVIGSIIVIL (SEQ ID NO: 15). In one embodiment the present invention contemplates a hydrophobic core protein comprising any seven contiguous amino acid residues in the sequence: FLIVIGSIIVIL (SEQ ID NO: 15). In one embodiment the present invention contemplates a hydrophobic core protein comprising any eight contiguous amino acid residues in the sequence: FLIVIGSIIVIL (SEQ ID NO: 15).

In one embodiment the present invention contemplates a hydrophobic core protein comprising any nine contiguous amino acid residues in the sequence: FLIVIGSIIVIL (SEQ ID NO: 15).

In one embodiment the present invention contemplates a hydrophobic core protein comprising any ten contiguous amino acid residues in the sequence: FLIVIGSIIVIL (SEQ ID NO: 15).

In one embodiment the present invention contemplates a hydrophobic core protein comprising any eleven contiguous amino acid residues in the sequence: FLIVIGSIIVIL (SEQ ID NO: 15).

In one embodiment the present invention contemplates a hydrophobic core protein comprising any twelve contiguous amino acid residues in the sequence: FLIVIGSIIVIL (SEQ ID NO: 15).

In one embodiment, the present invention contemplates a composition comprising a hydrophobic core wherein said hydrophobic core comprises two subunits $Z_1$ and $Z_2$ where one or both of the subunits is bound to a peptide X wherein X is (isoleucine) an aliphatic and aromatic amino acid with a negative hydrophobicity value and $Z_1$ is FLIV (SEQ ID NO: 23) and $Z_2$ is GSII (SEQ ID NO: 24).

A composition comprising an adhesive peptide having the sequence $K_3$AAAAABBAAK$_3$ (SEQ ID NO: 21) where Group A include aliphatic and aromatic amino acids with negative hydrophobicity values, Group B include small uncharged amino acids with slightly positive hydrophobicity values and, $K_3$ is a lysine tripeptide.

In one embodiment, $K_3$AAAAAK$_3$ (SEQ ID NO: 20) is a second functional motif. In one embodiment, $K_3$ABBAAK$_3$ (SEQ ID NO: 22) a preferred motif. In one embodiment, $K_3$AAAAABBAAK$_3$ (SEQ ID NO: 21) is a combined motif.

In one embodiment, the present invention describes a composition comprising an adhesive peptide comprising (or consisting of) a hydrophobic core wherein said hydrophobic core comprises (or consists of) FLIVI (SEQ ID NO: 16). In another embodiment said hydrophobic core further comprises $X_1$ operably linked to the N-terminus and the C-Terminus wherein $X_1$ consists of a dipeptide or a tripeptide. In one embodiment, said dipeptide comprises lysine-lysine. In another embodiment, said tripeptide comprises lysine-lysine-lysine.

In one embodiment, the present invention describes a composition comprising an adhesive peptide comprising (or consisting of) a hydrophobic core wherein said hydrophobic core comprises (or consists of) IGSII (SEQ ID NO: 17). In another embodiment said hydrophobic core further comprises $X_1$ operably linked to the N-terminus and the C-Terminus wherein $X_1$ consists of a dipeptide or a tripeptide. In one embodiment, said dipeptide comprises lysine-lysine. In another embodiment, said tripeptide comprises lysine-lysine-lysine.

In one embodiment, the present invention describes a composition comprising an adhesive protein comprising (or consisting of) a hydrophobic core wherein said hydrophobic core comprises (or consists of) FLIVIGSII (SEQ ID NO: 2).

In one embodiment, the present invention describes an adhesive protein comprising a hydrophobic core peptide operably linked to and at least one dipeptide or tripeptide, wherein said hydrophobic core peptide comprises $Z_2Z_1$FLIVIGSIIZ$_3Z_4Z_5$ (SEQ ID NO: 19) wherein $Z_1$ is phenylalanine or no amino acid and, if $Z_1$ is phenylalanine, then $Z_2$ is valine, $Z_3$ is valine or no amino acid, and if $Z_3$ is valine, then $Z_4$ is isoleucine and $Z_5$ is leucine. In one embodiment, said dipeptide comprises lysine-lysine. In another embodiment, dipeptide comprises glutamic acid-glutamic acid. In another embodiment said dipeptide comprises diaminopropionic acid-diaminopropionic acid. In another embodiment, said adhesive protein further comprises tandem repeats of said hydrophobic core and said dipeptide. In one embodiment, said tripeptide comprises lysine-lysine-lysine. In another embodiment, said tripeptide comprises glutamic acid-glutamic acid-glutamic acid. In another embodiment said tripeptide comprises diaminopropionic acid-diaminopropionic acid-diaminopropionic acid. In another embodiment, said adhesive protein further comprises tandem repeats of said hydrophobic core and said tripeptide. In one embodiment, said adhesive protein is selected from the group consisting of $E_3h_9E_3$, $K_3h_9F_3$, $E_3h_9K_3$, $K_3h_9K_3$, and $X_3h_9X_3$, wherein $h_9$=the hydrophobic core sequence FLIVIGSII (SEQ ID NO: 2); $K_3$=the tripeptide lysine-lysine-lysine, $E_3$=the tripeptide glutamic acid-glutamic acid-glutamic acid; and $X_3$=the tripeptide diaminopropionic acid-diaminopropionic acid-diaminopropionic acid. In another embodiment, said adhesive protein is selected from the group consisting of $(K_3h_9)_2K_3$ and $(K_3h_9)_3K_3$, wherein: $h_9$=the hydrophobic core sequence FLIVIGSII (SEQ ID NO: 2); and $K_3$=the tripeptide lysine-lysine-lysine.

In one embodiment, the present invention describes a method, comprising providing:
i) a protein comprising FLIVIGSII (SEQ ID NO: 2) attached to at least one tripeptide;
ii) a solution having an approximate pH 12; and contacting said protein with said solution under conditions that create an adhesive protein. In one embodiment said adhesive protein comprises a beta-sheet conformation. In another embodiment said beta-sheet conformation comprises an anti-parallel orientation. In another embodiment, said adhesive protein comprises a hydrophobic core stabilized by Van der Waals interactions. In another embodiment, said adhesive protein comprises a shear strength in the range between 0.5-5.0 MPa. In another embodiment, said adhesive protein comprises a viscosity in the range between 0.1-350 mPa·sec.

In one embodiment, the present invention describes a kit for the preparation of an adhesive comprising: a syringe having a first barrel, said first barrel filed with an aqueous solution of the peptide according to claim 1, buffered to maintain a pH between 6 and 7, and a second barrel, said second barrel filed with a base having a pH of approximately 12, wherein said first and second barrels are operably linked to a tip having a single lumen, wherein said lumen is in fluidic communication with said first and second barrels.

In one embodiment, the present invention describes an adhesive peptide comprising the sequence $K_3ABBAAK_3$ (SEQ ID NO: 22) wherein A comprises aliphatic and aromatic amino acids with negative hydrophobicity values, B comprises small uncharged amino acids with slightly positive hydrophobicity values and, K comprises a lysine tripeptide. In one embodiment, said A is selected from the group consisting of: Leu, Ile, Met, Val or phe and wherein said B is selected from the group consisting of: Gly, Ser and Ala.

In one embodiment, the present invention describes an adhesive peptide having the sequence $K_3AAAAAK_3$ (SEQ ID NO: 20) where A comprises aliphatic and aromatic amino acids with negative hydrophobicity values and, K comprises a lysine tripeptide.

DEFINITIONS

The term "adhesive protein", as used herein, refers to any amino acid sequence having sufficient adherent forces (i.e., hydrophobic, Van der Waals, ionic etc.) to resist a shearing force of approximately 0.25-5.00 MPa.

The term "hydrophobic core", as used herein, refers to any first amino acid sequence flanked by at least one second amino acid sequence, wherein the second amino acid sequence improves solubility or comprises ionically charged side chains. In a preferred embodiments, said hydrophobic core comprises: FLIVIGSII (SEQ ID NO: 2), FLIVI (SEQ ID NO: 16) and, IGSII (SEQ ID NO: 17).

The term "dipeptide", as used herein, refers to two, contiguous, identical amino acid residues.

The term "tripeptide", as used herein, refers to three, contiguous, identical amino acid residues.

The term "tandem repeat", as used herein, refers to any protein wherein the protein has a back-to-back repetition of a specific amino acid sequence. For example, the tandem repeat may include, but is not limited to, the back-to-back repetition of a hydrophobic core and at least one tripeptide. For example a tandem repeat may comprise, KKK-FLIVIGSII-KKK-FLIVIGSII (SEQ ID NO: 3).

The term "beta-sheet conformation", as used herein, refers to any tertiary protein structure where the protein forms overlapping layers, thus forming a beta-pleated sheet. Such beta-pleated sheets may reside in either a "parallel orientation" (symmetric amino and carboxyl termini or an "anti-parallel orientation" (asymmetric amino and carboxyl termini).

The term "shear strength", as used herein, refers to the force (MPa) required to break any first material (i.e., for example, an adhesive protein) adhered to second material (i.e., for example, wood).

BRIEF DESCRIPTION OF THE FIGURES

FIG. 13 presents sequences (SEQ ID NOs: 25-29, 7 and 31-33, respectively) of synthesized peptides (having hydrophobic cores of varied lengths) along with the masses, calculated pI values, and mean hydrophobicity at pH 7.0 and pH 12.0 of the same.

DETAILED DESCRIPTION

Figure 1:
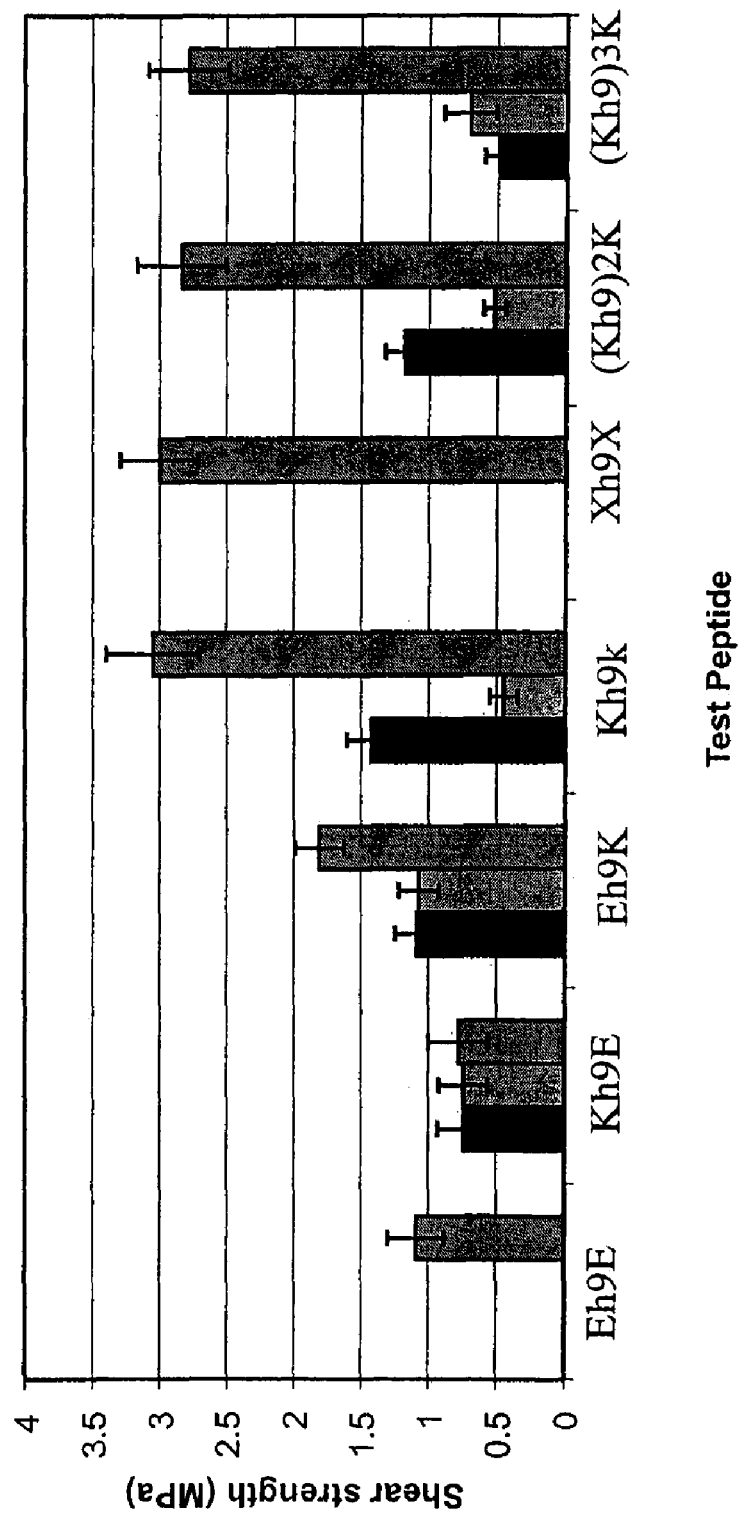
FIG. 1 presents exemplary shear strength measurements for different synthetic peptide embodiments and pH effects on their shear strength on wood. Specimens were pressed at 130° C. and 1.4 kg/cm$^2$ for 5 min. Black bars: pH 2.2; Light Grey: pH 6.8; Dark Grey: pH 12.

This invention relates to solid-phase peptide synthesis of short adhesive peptides based on a mixture of hydrophobic and β-sheet stacking interactions. In one embodiment, the peptide adhesive comprises a hydrophobic segment promoting rapid aggregation. In another embodiment, the peptide adhesive forms a network of interlocking strands.

The present invention contemplates designing protein adhesives at the peptide level that may be useful to design chemical reaction pathways of commercial proteins to improve adhesive performance. In another embodiment, peptide adhesives, via gelling properties, have potential application in pharmaceutical or medical area. In comparison to the embodiments described herein, the adhesive strength of a native soy protein based adhesives for plywood is in the range of 3.5-4.5 MPa for dry strength and 0.5 MPa for wet strength (Huang and Sun, 2000a,b). Modified soy protein adhesive on wood has about 6 MPa dry strength and 3.5 MPa wet strength (Sun et al. 2004), which is comparable to formaldehyde-based adhesives commonly used for wood products.

I. Peptide Design, Synthesis, and Characterization

The present invention contemplates novel peptide embodiments comprising from between 9 to 37 amino acid residues in length designed to include a nine-residue hydrophobic core FLIVIGSII ($h_9$) (SEQ ID NO: 2) FLIVI ($h_{5n}$) (SEQ ID NO: 16) or IGSII ($h_{5c}$) (SEQ ID NO: 17). In one embodiment, these peptides are derived from the full length IVS3 transmembrane segment from the human skeletal dihydropyridine-sensitive calcium channel that forms insoluble aggregates during freeze-drying (Grove et al., 1993). In one embodiment, the 9-residue IVS3 hydrophobic core comprises tripeptides including, but not limited to, lysine residues ($K_3$) or glutamic acid residues ($E_3$) yielding, for example, the sequences denoted as $E_3h_9E_3$ or $K_3h_9K_3$ (See, Table 1).

TABLE 1

Amino Acid Sequences Of Synthetic Peptides

| Peptide | Sequence | MW |
|---|---|---|
| $E_3h_9E_3$ | EEE-FLIVIGSII-EEE (SEQ ID NO: 4) | 1,748.9 |
| $K_3h_9E_3$ | KKK-FLIVIGSII-EEE (SEQ ID NO: 5) | 1,746.1 |
| $E_3h_9K_3$ | EEE-FLIVIGSII-KKK (SEQ ID NO: 6) | 1,746.1 |
| $K_3h_9K_3$ | KKK-FLIVIGSII-KKK (SEQ ID NO: 7) | 1,743.3 |
| $(K_3h_9)2K_3$ | KKK-FLIVIGSII-KKK-FLIVIGSII-KKK (SEQ ID NO: 8) | 3,084.1 |
| $(K_3h_9)3K_3$ | KKK-FLIVIGSII-KKK-FLIVIGSII-KKK-FLIVIGSII-KKK (SEQ ID NO: 9) | 4,424.8 |
| $X_3h_9X_3$ | XXX-FLIVIGSII-XXX (SEQ ID NO: 10) | 1,490.8 |

The shorthand notation used in Table 1 includes: $h_9$=the hydrophobic core sequence FLIVIGSII (SEQ ID NO: 2); $K_3$=the tripeptide lysine-lysine-lysine, $E_3$=the tripeptide glutamic acid-glutamic acid-glutamic acid; and $X_3$=the tripeptide diaminopropionic acid-diaminopropionic acid-diaminopropionic acid.

Although it is not necessary to understand the mechanism of an invention, it is believed that the L-lysines improve peptide solubility by adding positive charge to the peptide at neutral pH and serve as hydrophobic residues at elevated pH. In one embodiment, a peptide adhesive comprises an amino acid sequence containing the shortened lysine analog, 2,3-diaminopropionic acid ($X_3h_9X_3$).

In one embodiment, the lysine's R-group reduces hydrophobicity at approximately pH 12. In another embodiment, the peptide comprises two zwitterionic amino acid sequences containing both E and K including, but not limited to, $E_3h_9K_3$ and $K_3h_9E_3$.

In another embodiment, peptide adhesives comprise $K_3h_9K_3h_9K_3$, including, but not limited to, $(K_3h_9)_2K_3$ (SEQ ID NO: 11) and $(K_3h_9)_3K_3$ containing di- and tri-repeats of the $K_3h_9$ sequence motifs. At the pH extremes, it is believed that these peptide adhesives have different mean residue hydrophobicities due to the different ionization state of the $E_3$ and $K_3$ or $X_3$ tripeptide segments. Also, depending on whether these segments are located at the C- or N-terminus, the pKa values for the α-carboxyl or α-amino groups might be altered.

Although it is not necessary to understand the mechanism of an invention, it is believed that if like residues are clustered, the pKa's of the terminal α-carboxyl or α-amino groups (i.e. NH$_2$-KKK or EEE-COO) will be shifted toward pH extremes while if unlike residues are clustered (i.e. NH$_2$-EEE or KKK-COO), the pKa's of the terminal α-carboxyl or α-amino groups will be shifted toward neutral pH. The mean hydrophobicities ($\Delta G_{ave}$) and net charges of the test sequences at pH 2.2, 6.8 and 12.0 are shown in Table 2.

TABLE 2

Net charge and Mean Residue Hydrophobicity (H) for Test Peptides

| Peptide | Charge (pH 2.2) | $\Delta G_{ave}$ | Charge (pH 6.8) | $\Delta G_{ave}$ | Charge (pH 12.0) | $\Delta G_{ave}$ |
|---|---|---|---|---|---|---|
| -$h_9$- | 0 | 1.02 | 0 | 1.2 | 0 | 1.02 |
| $E_3h_9E_3$ | (+1) $h_9$ (−0.5) = 0.5 | 0.27 | (−2) $h_9$ (−4) = −6 | 0.31 | (−4) $h_9$ (−3) = −7 | 0.31 |
| $K_3h_9E_3$ | (+4) $h_9$ (−0.5) = 3.5 | 0.14 | (+4) $h_9$ (−4) = 0 | 0.16 | (−1) $h_9$ (−4) = −5 | 0.16 |
| $E_3h_9K_3$ | (+1) $h_9$ (+3) = 4 | 0.14 | (−2) $h_9$ (+2) = 0 | 0.16 | (0) $h_9$ (−4) = −4 | 0.16 |
| $K_3h_9K_3$ | (+4) $h_9$ (+3) = 7 | 0.01 | (+4) $h_9$ (+2) = 6 | 0.01 | (0) $h_9$ (−1) = −1 | 1.03 |
| $(K_3h_9)_2K_3$ | (+4) $h_9$ (+3) h (+3) = 10 | 0.17 | (+4) $h_9$ (+3) $h_9$ (+2) = 9 | 0.17 | (0) $h_9$ (0) h (−1) = −1 | 1.03 |
| $(K_3h_9)_3K_3$ | (+4) $h_9$ (+3) h (+3) $h_9$ (+3) = 13 | 0.24 | (+4) $h_9$ (+3) $h_9$ (+3) $h_9$ (+2) = 12 | 0.24 | (0) $h_9$ (0) h (0) h (−1) = −1 | 1.03 |
| $Xh_9X$ | (+4) $h_9$ (+3) = 7 | 0.01 | (+4) $h_9$ (+2) = 6 | 0.01 | (0) $h_9$ (−1) = −1 | 0.66 |

Table 2 presents the Net Charge and Mean Residue Hydrophobicity ($\Delta G_{ave}$ in kCal/mol) for several peptide embodiments at the different test pH values. The $\Delta G_{ave} = \Sigma \Delta G$ residue/residue number. $\Delta G$ residue values are taken from modified Wimley-White scale (Jayasinghe et al., 2001).

Although it is not necessary to understand the mechanism of an invention, it is believed that net charge and mean residue hydrophobicity change significantly as a function of pH values. In one embodiment, peptide adhesives comprise an altered adhesive strength at different pH values. Hydrophobicity may be modified by the composition and size of acyl side chains. Many amino acids comprise acyl side chains, including, but not limited to, lysine, leucine or isoleucine.

The acyl side chain of the lysine contains the same number of carbons as the side chains of leucine and isoleucine. The lysine chain is linear while leucine and isoleucine are branched. The linear structure of the lysine acyl side chain would be expected to be more hydrophobic than either of leucine or isoleucine. However, the presence of the uncharged primary amine, with its partially polarizable lone pair of electrons on nitrogen and hydrogens, would generate a dipole thus decreasing the overall hydrophobicity of the amino acid. Since there are no published values for the hydrophobicity of lysine at pH 12.0 the value for leucine was selected. Based on the modified Wimley-White scale (Jayasinghe et al., 2001), the 2,3-diaminopropionic acid residue, with its $CH_2$—$NH_2$ side chain, should possess a $\Delta G_{residue}$ value intermediate to that of alanine (—$CH_3$; –0.5 Kcal/mole) and valine (—CH—$(CH_3)_2$; 0.46 Kcal/mole). Taking into account the electron rich lysine nitrogen atom, at pH 12 lysine might be expected to have a value of approximately –0.1 Kcal/mole. In a similar manner, the hydrophobicity value of glutamine was used for glutamic acid at low pH levels. Of particular note, large changes in both charge and hydrophobicity are seen for the peptides that have cationic sequences at both termini. At pH 2.2, the $K_3h_9K_3$ and $X_3h_9X_3$ sequences, have a net positive charge of nearly +7, while at high pH the peptides charges are –1. At these high pH levels, the lysines and 2,3-diaminopropionic acids containing peptides become significantly more hydrophobic.

The peptides $K_3h_9K_3$ and $X_3h_9X_3$ at high pH have calculated mean residue hydrophobicities of 1.03 and 0.66 Kcal/mole, respectively. The $X_3h_9X_3$ peptide has a lower mean residue hydrophobicity that is intermediate to that of the lysine and the glutamic acid adducted $K_3h_9K_3$ and the $E_3h_9E_3$ sequences.

In one embodiment, the aforementioned FLIVIGSII (SEQ ID NO: 2) hydrophobic core, linked to the three lysine residues ($K_3h_9K_3$), was used as a departure point for the alteration of the hydrophobic core length. That is to say, in select embodiments, new peptides with a hydrophobic core of 5, 7, 11, and 12 amino acid residues in length were designed and synthesized (as shown in FIG. 13).

These core peptides were then flanked by tripeptides of lysine. To increase the length of hydrophobic core, two hydrophobic amino acid (valine and phenylalanine) or three hydrophobic amino acids (valine, isoleucine, and leucine) were incorporated to the nine-amino acid residue hydrophobic core FLIVIGSII (SEQ ID NO: 2) and yielded peptides designated as $K_3h_{11}K_3$ and $K_3h_{12}K_3$, respectively.

In some embodiments the 11 and 12-residue cores were derived from larger segments within the IVS3 segment. In some embodiments, the nine-amino acid residue hydrophobic core was shortened by removing two isoleucine residues, thereby, yielding a peptide denote as $K_3h_7K_3$. In some embodiments, the five amino acid residue segments from either the C- or N terminus of $h_9$ were selected and synthesized. They are denoted as $K_3h_{5c}K_3$ and $K_3h_{5n}K_3$, respectively (as shown in FIG. 13).

In another embodiment, $K_3h_{5c}K_3$ and $K_3h_{5n}K_3$ were modified such that these two sequences were flanked with only two lysine residues. These sequences were designated as $K_2h_{5n}K_2$ and $K_2h_{5c}K_2$, respectively.

In one embodiment, $KAE_{16}$, a peptide containing alternating polar and nonpolar residues and known to adopt β-sheet structure at both neutral and high pH was also synthesized and tested.

Figure 6:
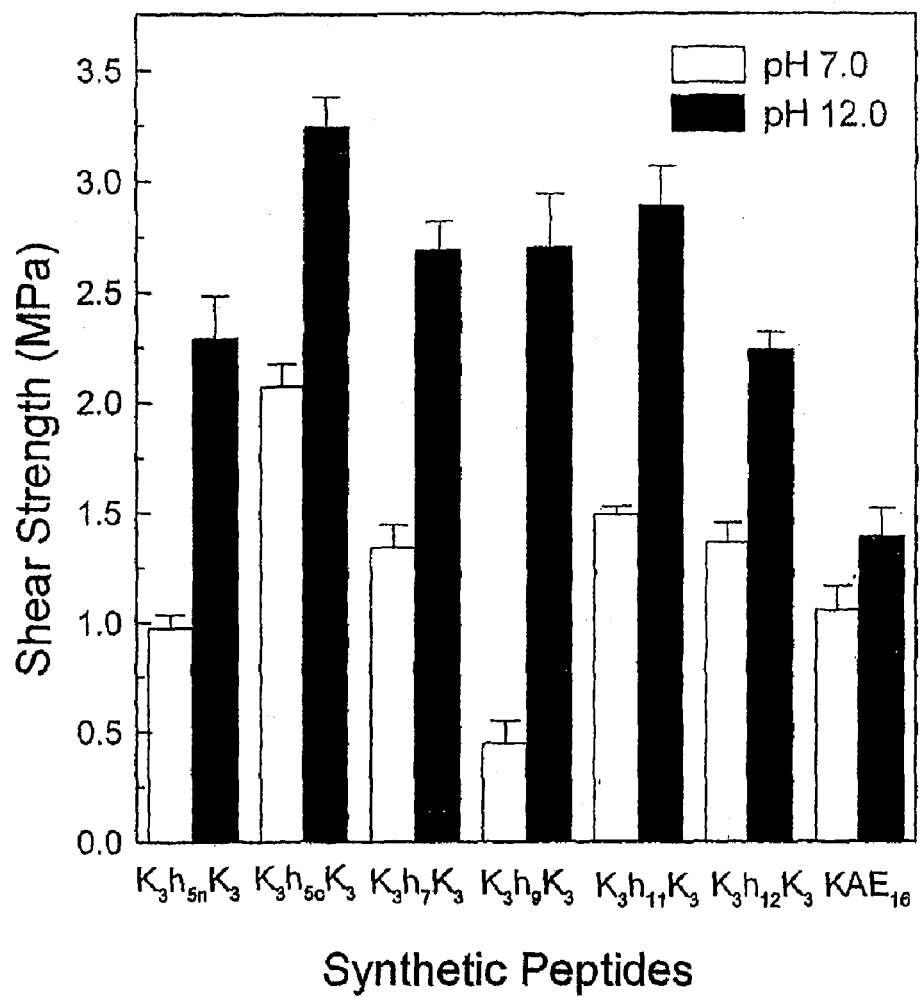
FIG. 6 illustrates the adhesive strength of various peptides at pH 7 (empty bar) and pH 12 (solid bar).

The sequences of synthesized peptides (having hydrophobic cores of varied lengths) along with their masses, calculated pI values, and mean hydrophobicity at pH 7.0 and pH 12.0 are presented in FIG. 13. The adhesive properties of these same peptides were measured at a pH of 7.0 and 12.0 (as shown in FIG. 6).

The peptides, set out in FIG. 13, at pH 12 all showed significant increased in hydrophobicity (more negative values) than those at pH 7. While it is not intended that the present invention be limited to any specific mechanism (nor is an understanding of an underlying mechanism a prerequisite to practice the present invention) these data may be explained by the deprotonization of the lysine residues common to all the adhesive peptides. That is to say, at pH 12 peptides with five-amino acid residue hydrophobic core $K_3h_{5c}K_3$ and $K_{2h5c}$ having the lowest mean hydrophobicity value of –0.69 Kcal/mol, were the most hydrophobic among the peptide prepared; whereas $KAE_{16}$ had the highest mean hydrophobicity value of +0.40 kcal/mol and the least hydrophobic character.

II. pH Effect on Adhesive Strength of Synthetic Peptides

The adhesive properties of the seven synthetic peptide embodiments shown in Table 1 were tested at pH values of 2.2, 6.8, and 12.0 using a hot-pressing temperature of 130° C. and a pressure of 1.4 Kg/cm². By measuring the adhesive or shear strength of the peptides under these conditions, the contributions of hydrophobicity and net charge to adhesive strength were ascertained. FIG. 1 shows the shear strengths of 4% w/w peptide solutions as a function of the pH. The anionic peptide, $E_3h_9E_3$ was insoluble at the two lower pH values thus precluding those adhesive strength analyses. At pH 12.0, $E_3h_9E_3$ displayed weak adhesive properties showing shear strength of only 1.09±0.21 MPa. The adhesive strength of a zwitterionic species (i.e., for example, $K_3h_9E_3$), comprising similarly charged amino terminus cationic residues and C-terminus anionic residues are only weakly adhesive at all pH values.

This peptide at high pH should be strongly amphiphilic with the highly charged C-terminus (–4) and the neutral hydrophobic N-terminus and hydrophobic core. Other zwitterionic species (i.e., for example, $E_3h_9K_3$) which have a reduced net charge at both termini, show a similar but slightly stronger adhesive strength at pH 2.2 and 6.8 compared to $K_3h_9E_3$. At high pH (i.e., for example, 12.0), the adhesive strength of $E_3h_9K_3$ was greatly enhanced, 1.81±0.18 MPa. At this pH, the peptide would have a net charge of –4 with one of the negative charges at the C-terminus of the peptide and a charge of –3 at the N-terminus. Although it is not necessary to understand the mechanism of an invention, it is believed that charge redistribution over the whole molecule reduces the amphiphilic character of the peptide and improves the adhesive properties.

In one embodiment, the sequence $K_3hK_3$ displays modest adhesive strength at low pH and minimal strength at neutral pH. (FIG. 1). In another embodiment, at high pH the peptide is quite hydrophobic, thereby increasing the peptide adhesive strength to approximately 3.05±0.35 MPa. Although it is not necessary to understand the mechanism of an invention, it is believed that pH-induced changes in mean residue hydrophobicity from 0.01 at pH 6.8 to 1.03 at pH 12 might play a role in increased in adhesive strength under the hot-press condition. For example, at pH 12 there is one negative charge associated with the C-terminus of the peptide. When the peptide was resynthesized as the carboxamide (i.e., to remove the C-terminal negative charge) the peptide becomes completely uncharged at pH 12. However, no difference was seen in the adhesive strength of the −1 and 0 charge $K_3h_9K_3$ peptides.

The data further suggests that as the pH increases from 2.2 to 6.8, C-terminal carboxyl group deprotonation introduces a negative charge to the highly cationic peptide. In one embodiment, deprotonation results in a net charge of the C-terminus from +3 to +2, thereby having a net decrease from +7 to +6. Although it is not necessary to understand the mechanism of an invention, it is believed that changes in net charge are not a factor for the reduced adhesive strength observed at neutral pH. If this were true, the peptide in the low pH solution should show weaker adhesive strength based on Coulombic repulsion of the like charges.

The generation of the new C-terminal negative charge at neutral pH might be introducing a small change to the secondary structure of the peptide that interferes with the packing of the peptides during the hot-press treatment.

A bis-trilysine adducted sequence replaced six lysine residues with either two tri-histidines (i.e., for example, $H_3h_9H_3$; SEQ ID NO: 12) or two tri-arginines (i.e., for example, $R_3h_9R_3$; SEQ ID NO: 13). $H_3h_9H_3$ failed to produce good adhesives at the three pH values used to test the $K_3h_9K_3$ sequence. The $H_3h_9H_3$ derivative was insoluble at all pH values and the $R_3h_9R_3$ sequence was not fully ionized at pH 12.0. Raising the pH to a value>14 where the guanido amine of arginine would be deprotonated did not seem commercially acceptable.

Two longer peptides were designed to test whether peptide length had any effect on adhesive strength. Peptides $(K_3h_9)_2K_3$, 26-residues and $(K_3h_9)_3K_3$, 37-residues, displayed adhesive strengths of 2.83±0.33 and 2.78±0.30, respectively. These two different tandem repeat sequences showed no further increase in adhesive strength over the $K_3h_9K_3$ peptide indicating that added length does not improve the adhesive properties.

The adhesive strength of all peptides set out in FIG. 13 are presented in FIG. 6. For this group of adhesive peptides, all adhesives prepared at pH 12.0 demonstrated higher adhesive strength than those prepared at pH 7.0. Adhesives prepared at pH 12.0 usually also had wood failure around 15%, whereas those at pH 7.0 had a value around 5%, suggesting that adhesives made from peptides at pH 12.0 had relatively strong adhesive cohesion after curing. The peptides presented in FIG. 13 all contain lysine residues.

While it is not intended that the present invention be limited to a specific mechanism, the pH-induced lysine depronation made the peptides more hydrophobic and this likely contributed to increased adhesive strength. In contrast, substituting diaminopropionic acid with a shortened (—$CH_2$—$NH_2$—) side chain showed little contribution of the lysines to overall adhesive strength. Therefore, the length of a peptide hydrophobic core is an important factor in adhesive strength.

Using a nine-amino acid residue hydrophobic core as a reference point, the adhesive strength of a given peptide increases as the number of amino acid residues in the hydrophobic core increases up to a core length of eleven amino acid residues which exhibits an adhesive strength of 2.9 Mpa. That is to say, this eleven amino acid residue hydrophobic core adhesive maxima is evidenced by the decrease in adhesive strength when the hydrophobic core is increased to twelve-amino acid residues.

For peptides with shortened hydrophobic cores, as compared to FLIVIGSII (SEQ ID NO: 2), the peptide with a seven-amino acid residue-hydrophobic core showed similar adhesive strength to the peptide with a nine-amino acid residue core. Adhesives from the peptide with a five-amino acid residue hydrophobic core ($K_3h_{5c}K_3$) demonstrated adhesive strength of 3.2 Mpa. In contrast, adhesives from the peptide with the five-amino acid residue core $K_3h_{5n}K_3$ showed an adhesive strength of 2.3 MPa.

The adhesives from those peptides showed a 40% difference in adhesive strength even though they have the same length of hydrophobic core. That is to say, adhesive strength is dependent on more that just the absolute length of the hydrophobic core. More specifically, the amino acid composition of the peptide appears to modulate the peptides' hydrophobic properties and, thereby, account for variations in adhesive strength. For example, peptide $K_3h_{5c}K_3$ is more hydrophobic (with low $\Delta G_{avg}$ value) and has a higher adhesive strength than peptide $K_3h_{5n}K_3$. These data demonstrate there is an inverse relationship between peptide hydrophobicity and adhesive strength.

As described above, the peptide $K_3h_9K_3$ had the highest adhesive strength among a series of peptides, with the FLIVIGSII (SEQ ID NO: 2) hydrophobic core, synthesized with different terminal clusters. The physio-chemical properties of peptide $K_3h_9K_3$ include: i) hydrophobicity and ii) a stable beta sheet structure.

The contribution of a peptides beta sheet structure on adhesive strength was documented as follows. The peptide $KAE_{16}$, which has a sequence containing alternation polar and nonpolar residues and known to adopt stable beta sheet structure at both pH 7.0 and 12, was evaluated. Peptide $KAE_{16}$ gave a relatively low adhesive strength of 1.39 MPa at pH 12 and a even lower value of 1.06 MPa at pH 7.

Figure 14:
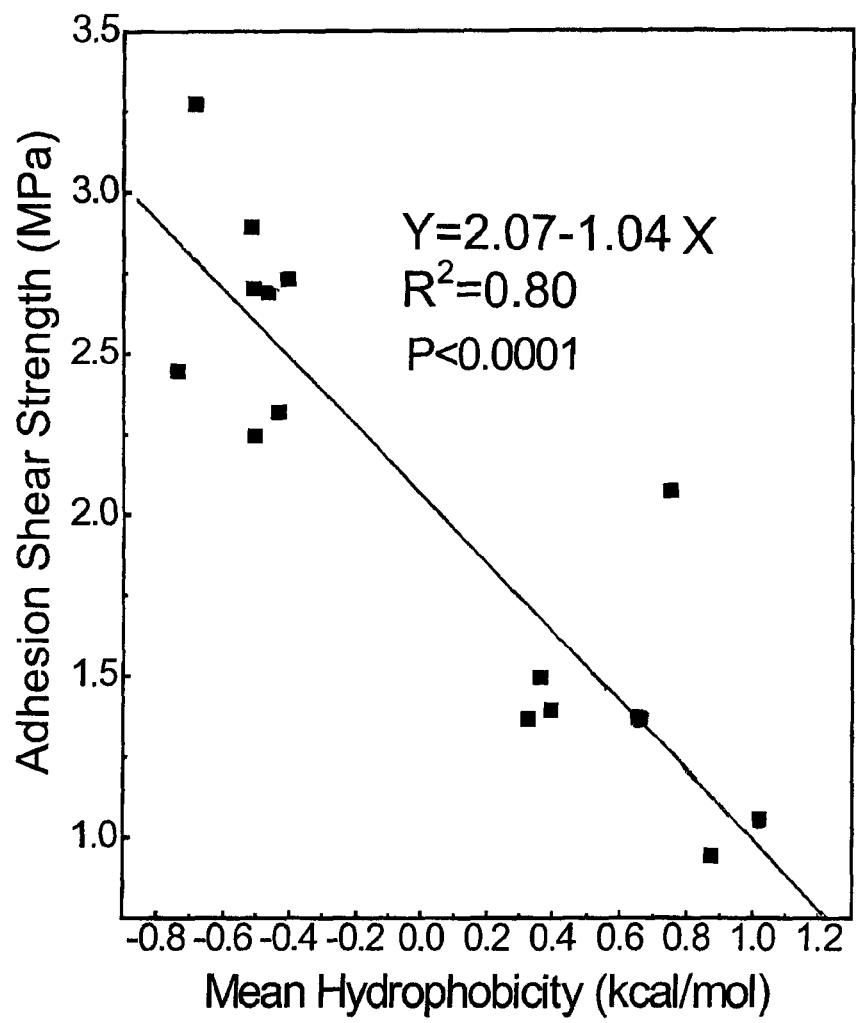
FIG. 14 presents a graph showing the correlation between peptide hydrophobicity and adhesive strength.

The contribution of peptide hydrophobicity on adhesive strength was documented as follows. Adhesive strength from the tested peptides at both pH 7.0 and pH 12.0 were plotted against their corresponding mean hydrophobicity and a linear regression statistical method was used to analyze these data. Significantly linear negative correlation with P<0.0001 and R of 0.80 was found between peptide adhesive strength and mean hydrophobicity (see, FIG. 14). Once again, while it is not intended that the present invention be limited to any specific mechanism, these data prove that hydrophobicity accounts for 80% of the variability in the adhesive strength for a given peptide.

For peptides with a five-amino acid hydrophobic core, the adhesive strength for peptides flanked with two lysine residues showed different behavior from those flanked with three lysine residues, depending on the amino acid composition of the hydrophobic core. Specifically, adhesive from peptide $K_2h_{5n}K_2$ had adhesive strength of 2.73 MPa higher than that of 2.29 MPa from peptide $K_3h_{5n}K_3$. Peptide $K_2h_{5c}K_2$ showed adhesive strength of 2.40 MPa, which was lower than that of 3.24 MPa from peptide $K_3h_{5c}K_3$, notwithstanding the fact that these peptides have the same mean hydrophobicity value.

These observations on the effect of: i) hydrophobic core length, ii) beta structure, iii) hydrophobicity, iv) flanking peptide sequences, v) pH, and vi) peptide solubility may be manipulated to design a peptide with a desired adhesiveness that will maximize performance within a given environment.

III. Cationic Residue-Induced Hydrophobicity

The above data shows that, at pH 12, lysine residues become quite hydrophobic. One potential explanation for this increased hydrophobicity involves increased van der Waals forces. To test this hypothesis, a synthetic adhesive protein comprising a truncated lysine analog 2,3-diaminopropionic acid (DAP) was employed. As shown in Table 2, the $X_3h_9X_3$ peptide has an average residue hydrophobicity intermediate to that of $K_3h_9K_3$ at low and high pH values. Due to the expense of making this compound, adhesive strength was tested only at pH 12.0. As shown in FIG. 1, the 130° hot press adhesive strength was measured as 3.0±0.29 MPa. This value is statistically identical to that for the $K_3h_9K_3$ sequence tested under identical conditions. The increased hydrophobicity seen in $K_3h_9K_3$ at elevated pH is not adding significantly to the adhesive strength of the sequence. However, this result does not eliminate the contributions of the hydrophobic core segment to both a minimum hydrophobicity threshold and the induction of β-structure.

IV. Viscosity

The rheological behavior of the peptides solutions was affected by pH in pure water (Table 3).

TABLE 3

Viscosity (mPa · s) Of Synthetic Peptide Under Different pH Conditions

| Peptide | pI | pH 2.2 | pH 6.8 | pH 12 |
|---|---|---|---|---|
| $E_3h_9E_3$ | 3.7 | n.a. | n.a. | 20 |
| $K_3h_9E_3$ | 6.3 | 210 | 305 | 20 |
| $E_3h_9K_3$ | 6.3 | 190 | 245 | 20 |
| $K_3h_9K_3$ | 10.7 | 20 | 20 | 290 |

(Synthetic Peptide Concentration of 4%,@20 rpm, and RT)

The peptide $E_3h_9E_3$ was insoluble below and somewhat above its pI thereby preventing viscosity measurements. The viscosity was highest for all other peptides at pH values close to their calculated pIs. In the case of the zwitterionic peptides (i.e., for example, $K_3h_9E_3$ and $E_3h_9K_3$), viscosities of 305 and 245 mPa·sec were recorded at pH 6.8. These sequences have highly charged ends of opposite charge that could adopt antiparallel alignments that would lead to charge neutralization. The increase in viscosity for these sequences near their pI values does not appear to be related to either change in the mean residue hydrophobicity or adhesive strength. Adhesive strength of $E_3h_9K_3$, for example, reached it highest value at pH 12, where its viscosity was at a minimum value of 20 mPa·sec. The zwitterionic peptides also show considerable viscosity at pH 2.2; a value well below their pI values. At pH 2.2, $K_3h_9E_3$ and $E_3h_9K_3$ have a more amphipathic character with most of the charge found at one end of the molecule. The net charge of these molecules is 3.5 and 4 for $K_3h_9E_3$ and $E_3h_9K_3$, respectively (Table 2). At pH 12.0, the peptides have net charges of −5 and −4, yet do not associate to change viscosity. It is possible that at low pH the amphipathic forms of the zwitterionic peptides adopt unique structures or conformers that promote association.

The $K_3h_9K_3$ peptide displays a very different profile with regard to viscosity, hydrophobicity and adhesive strength. $K_3h_9K_3$ shows no propensity to aggregate at pH values of 2.2 or 6.8. Only at pH 12, a value above its calculated pI of 10.7, does the peptide solution become viscous. At this pH, the peptide has a net charge of −1 and a dramatically elevated mean residue hydrophobicity of 1.03. Although it is not necessary to understand the mechanism of an invention, it is believed that peptide aggregation forces for this sequence is different from that seen with the zwitterionic species. Only in the case of $K_3h_9K_3$ does the increase in viscosity correlate positively with an increase in hydrophobicity and adhesive strength. The adhesive strength observed for this sequence is substantially higher than that seen for either zwitterionic peptide.

V. Press Temperature And Adhesive Strength

Figure 2:
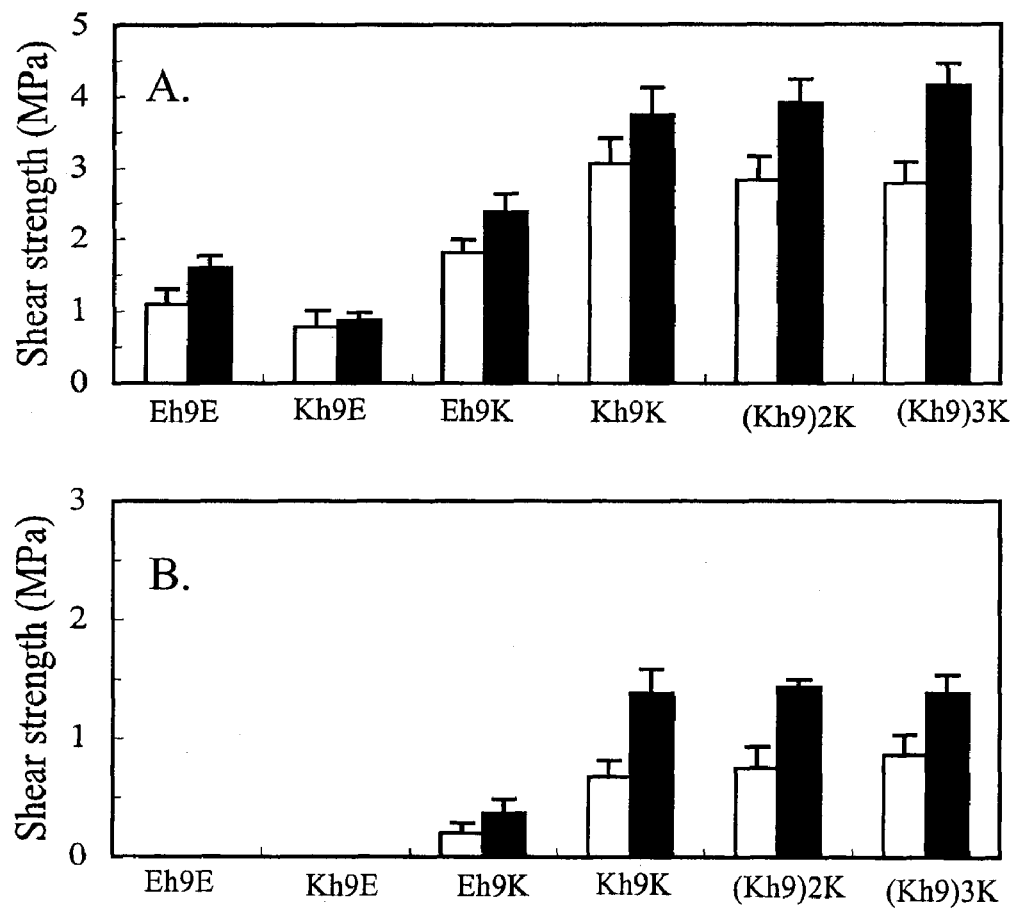
FIG. 2 presents exemplary data regarding press temperature on adhesive strength of synthetic peptide embodiments. Shear strengths were measured at pH 12. Specimens were pressed at 130° C. (white) or 170° C. (black) and 1.4 kg/cm$^2$ for 5 min. A, dry shear strength; B, wet shear strength.

Hot-pressing is generally used with synthetic wood glues and adhesives to increase curing rate and bonding strength. The adhesive strengths of peptides at pH 12 were measured at two hot press temperatures (FIG. 2A). These temperatures are well within the range used commercially in the production of various plywood materials. The dry shear strength of dried peptides at pH 12 at 170° C. are significantly increased over that seen at 130° C.

In one embodiment, synthetic adhesive peptides selected from the group comprising $E_3h_9K_3$, $K_3h_9K_3$, $(K_3h_9)_2K_3$, and $(K_3h_9)_3K_3$ showed increased shear strengths of 2.39±0.24, 3.74±0.38, 3.91±0.33 and 4.15±0.3, respectively. Press temperature is known to have marked effects on water evaporation, immobilization of adhesive molecules, and the interaction between adhesive and adherent, thereby improving the adhesive performance of the final products (Zhong et al., 2002, Yu and Deming, 1998; and Yamamoto et al., 2000). Further, the adhesive strength of synthetic adhesive peptides, as contemplated by the present invention (i.e., for example, $K_3h_9K_3$) approaches that reported for isolated soy protein adhesives (SPI) (Huang and Sun, 2000a,b). The adhesive strength of the $K_3h_9K_3$ peptide at pH 12 in $D_2O$ was also determined.

Deuterium oxide was added to try and assess the contributions of hydrogen bonding and the hydrophobic effect on the overall strength of the adhesive. The deuterium oxide had little effect on the adhesive strength, yielding a value of 2.7±0.33 (data not shown) at a hot press temperature of 130 (° C. The minimal effect observed for the adhesive strength of $K_3h_9K_3$ in the presence of $D_2O$ at pH 12 suggests that neither hydrophobic interactions nor hydrogen bonding were affected to any great extent. 10 In FIG. 2B, the shear strengths of the peptide adhesives at pH 12 are presented after immersion in water for 48 hr.

This value is termed "wet" shear strength and is a predictor of how glued wood products would behave after being exposed to environmental elements. $E_3h_9E_3$ and $K_3h_9E_3$ prepared at either temperature fall apart during the immersion step. $E_3h_9K_3$ showed a wet strength of 0.37±0.12 which is only 15% that of the dry 170° C. pressed sample. The $K_3h_9K_3$, $(K_3h_9)_2K_3$ and $(K_3h_9)_3K_3$ had wet strengths of 1.38±0.2, 1.43±0.06 and 1.38±0.15, respectively. These samples retained more than 33% of the dry 170° C. pressed shear strength. If the wetted samples are allowed to completely dry the shear strength returns nearly to that observed prior to wetting (data not shown).

VI. Shear Strength and Viscosity Versus Peptide Concentration

Figure 3:
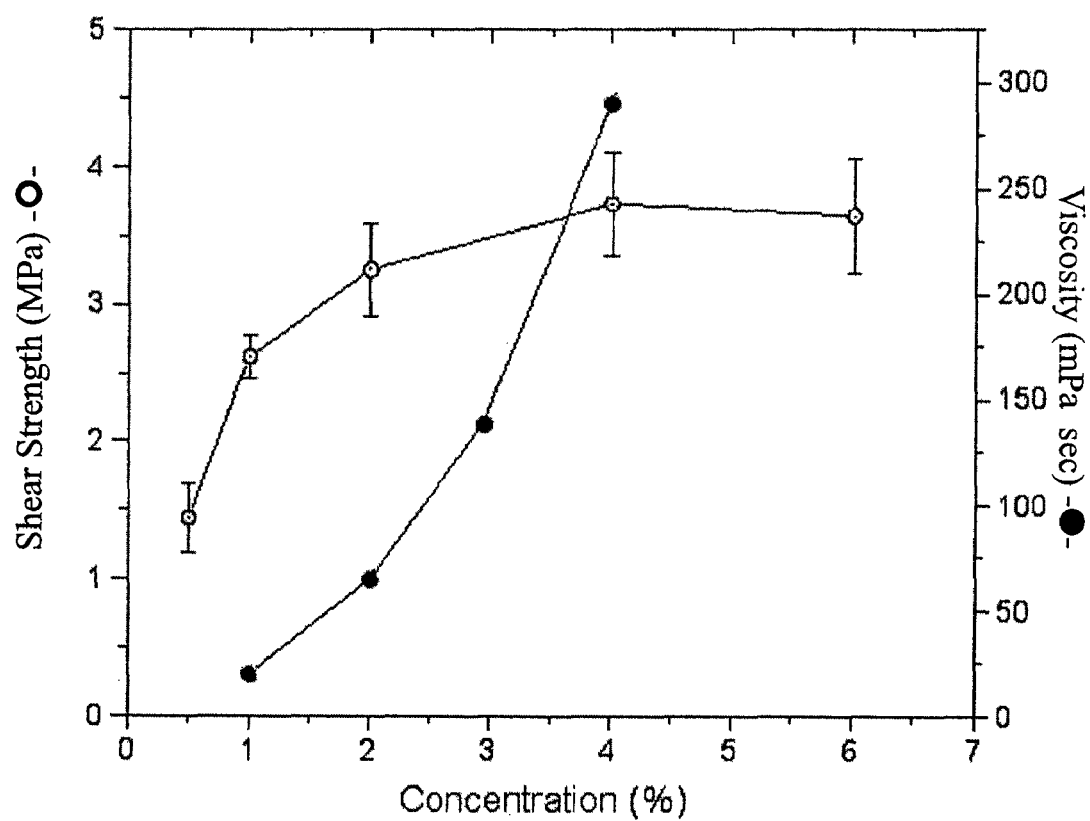
FIG. 3 presents exemplary data regarding peptide concentration dependence for $K_3h_9K_3$ on adhesive strength and viscosity at pH 12. The peptide concentrations tested in one or more method were 2.87 mM (0.5%), 5.7 mM (1%), 11.5 mM (2%), 17.2 mM (3%) 23 mM (4%) in $H_2O$/NaOH solution. Specimens were pressed at 170° C. and 1.4 kg/cm$^2$ for 5 min.

In one embodiment, an adhesive peptide (i.e., for example, $K_3h_9K$) was tested at different concentrations at 170° C. for changes in viscosity and shear strength. As shown in FIG. 3, the shear strength increased with concentrations up to a limit of approximately 3.7 MPa at a 4% concentration. Further increases in concentration did not improve shear strength.

Viscosity, on the other hand, increased at all concentrations tested. The viscosity dependence on concentration is clearly not linear. Comparing the viscosity at 4% to that measured at 2% reveals greater than a four-fold decrease in the viscosity at half the concentration. Since the technique used to measure viscosity does not yield kinetic data, it is not possible to determine the order of the aggregation process that increases viscosity. At best it appears that aggregation is not a single order process. The adhesive strength apparently plateaus at a 4% concentration.

Although it is not necessary to understand the mechanism of an invention, it is believed that the relationship between increases in viscosity and increases in adhesive strength is not clear-cut. For example, from a teleological perspective, peptide aggregation should enhance adhesive strength: the greater the peptide-peptide interactions the greater the shear strength. It is further believed that, a limit might be reached where the peptides interact almost exclusively with each other, rather than the surfaces being glued.

VII. Circular Dichroism

CD experiments, which actively monitor the intermolecular folding and intermolecular sheet assembly of peptide, when combined with rheology experiments, which actively monitored the self-assembly of the peptide into a gel scaffold, form a clear image of how material properties can be attributed to molecule folding and consequent assembly mechanism. Schneider et al. (2002).

Figure 4:
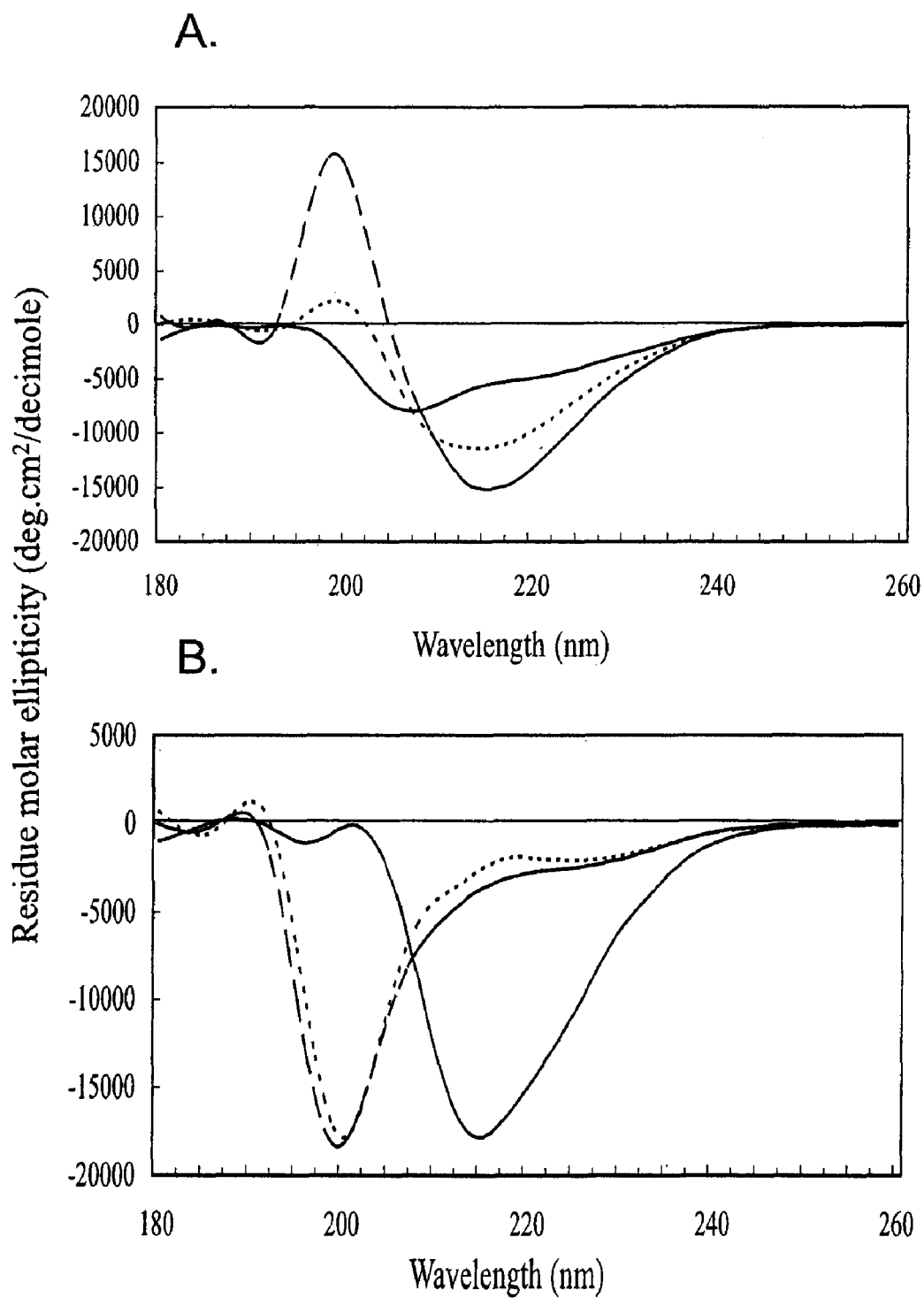
FIG. 4 presents exemplary data regarding circular dichroism spectra of soluble synthetic peptide $E_3h_9K_3$ (Panel A) and $K_3h_9K_3$ (Panel B). Peptide concentration was 250 Spectra were measured at pH 2.2 (shaded), pH 6.8 (broken line), and pH 12 (solid line), respectively, from 260 nm to 180 nm.

To understand what secondary structural properties of the peptides affect adhesive strength, dilute solutions $E_3h_9K_3$ and $K_3h_9K_3$ peptides at pH 12, were analyzed using circular dichroism (CD) for solution samples. Dilute solutions were used to minimize light scattering that occurs with the gelled samples at higher concentrations. FIG. 4A shows that the $E_3h_9K_3$ peptide adopts a classical anti-parallel β-sheet structure at pH 6.8 and also at pH 2.2, but to a lesser extent. At pH 6.8 this peptide is zwitterionic with a balanced −2 at the N- and +2 at C-termini, respectively. In an anti-parallel orientation, the oppositely charged ends can interact optimally. At pH 2.2, the peptide is not zwitterionic having +1 and +4 charges at the N- and C-termini, respectively. At pH 12, where the adhesive strength is at its highest, the peptide has a net negative charge of −4 and appears to be unstructured. In the case of $E_3h_9K_3$, beta structure in solution does not appear to be a requirement for its adhesive properties.

The $K_3h_9K_3$ peptide (FIG. 4B), however, does appear to have a structural component associated with increased adhesive strength. At pH 2.2 and pH 6.8, where the peptide is positively charged, the $K_3h_9K_3$ spectra show a predominantly random coil structure, while at pH where the peptide carries no net charge, a more β-like structure is observed. Clearly, pH conditions that promote a more ordered structure, enriched in β-sheet, dramatically increase adhesive strength. Nearly identical CD spectra were obtained at the three different pH values for the shortened lysine analog 2,4-diaminopropionic acid containing sequence, $X_3h_9X_3$ (data not shown). At the low and neutral pH random structure predominated however at elevated pH β-structure was observed.

It is believed that, upon drying (removing water molecules), the strength of the hydrogen bonds would increase due to a decrease in the concentration of competing hydrogen bond donating water molecules. Increasing the temperature of $K_3h_9K_3$ (250 µM) from 25° C. and 75° C., however, did not alter the CD spectra at pH 12 (not shown data). The results indicate that the conformation of $K_3h_9K_3$ peptide at pH 12 is resistant to change. A strengthening of the intermolecular interactions would help stabilize the beta-like structure during the heating and pressing steps.

VIII. Fourier Transform Infrared Spectroscopy (FTIR) Studies

Figure 5:
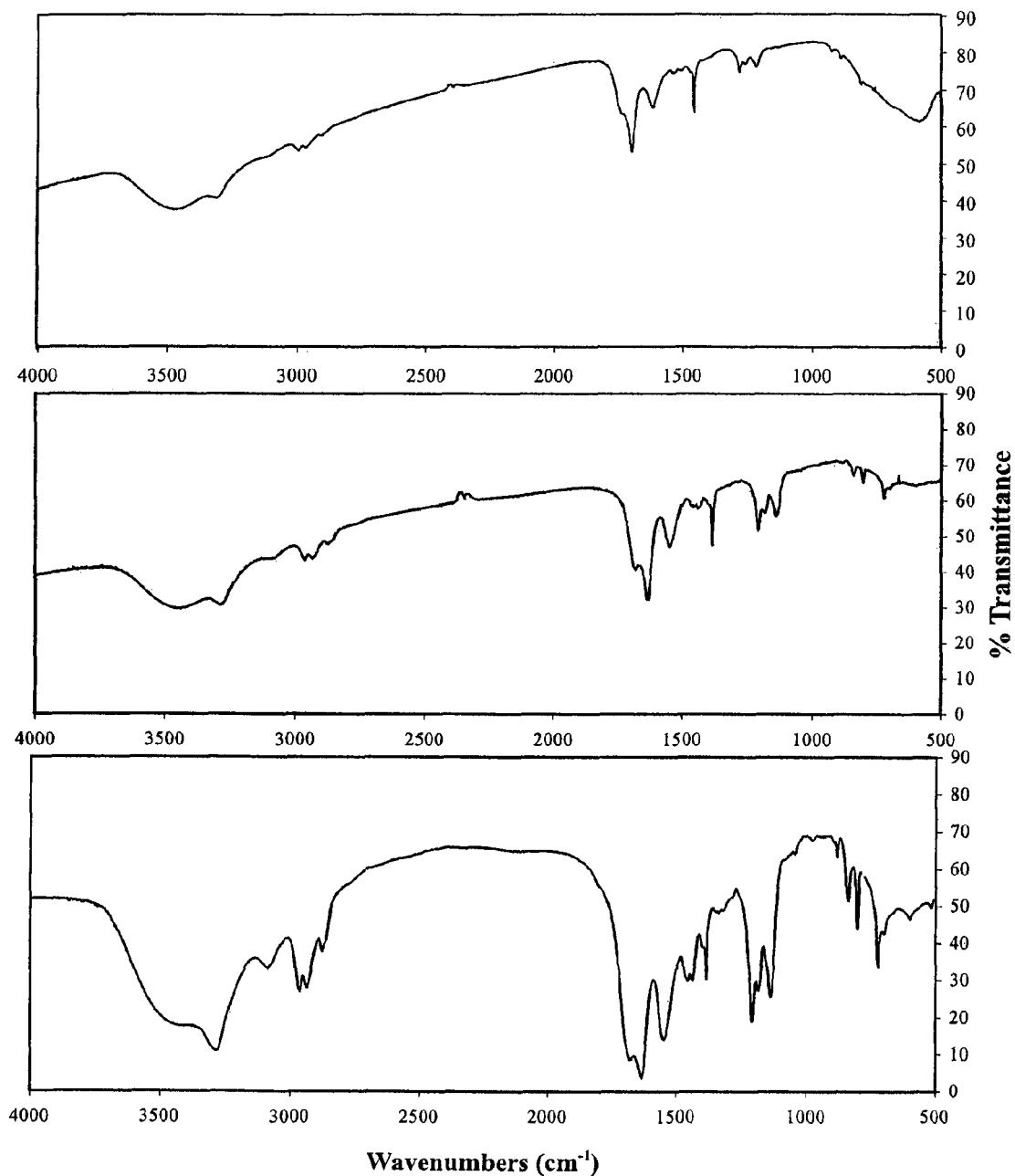
FIG. 5 presents exemplary Fourier Transform Infrared Spectroscopy (FTIR) data from harvested 4% $K_3h_9K_3$ after drying under control and press conditions prepared in $H_2O$ (black) at pH 12, at RT without pressure (top), 130° C. without pressure (middle) and 130° C. with pressure (bottom).

The FTIR spectra of the dry $K_3h_9K_3$ samples prepared using different temperatures and pressing conditions are seen in FIG. 5. All these spectra show characteristic amide I (1680 cm1), II (1548 cm$^{-1}$), and III (1206 cm$^{-1}$) stretches suggest the presence of an antiparallel β-sheet conformation. The result on the dried material indicate that the conformation of the $K_3h_9K_3$ peptide formed in solution at pH 12 is highly resistant to change. Even at elevated temperatures and desiccation, conditions that would usually denature a peptide, the β-like structure remains intact.

In one embodiment, the $K_3h_9K_3$ Amide I peak is split in β sheets and appears at 1680 cm$^{-1}$ and 1633 cm$^{-1}$ but the peak at 1680 cm$^{-1}$ weakens when going from hot press conditions to room temperature when comparing preparation techniques. This result indicates that there may be less β-sheet structure in samples prepared at either room temperature or 130° C. without pressure. In addition, the Amide II peak appears at 1548 cm$^{-1}$ is weaker in both the 130° C. no pressure and room temperature prepared samples.

The Amide III peak appears at 1206 cm$^{-1}$ is strongest in the hot press sample whereas the sample prepared at 130° C. without pressure gives a band of lesser intensity and the room temperature sample has only a weak band. This can be observed by internal ratios of intensities. This data can be seen in FIG. 5 and Table 4.

TABLE 4

Absorbance Ratios of Amide I, II, and III regions.

| | Amide 1 1681/cm | Amide 1 1633/cm | Amide 2 1548/cm | Amide 3 1207/cm | Internal Peak 1384/cm |
|---|---|---|---|---|---|
| Hotpress 130° C. H$_2$O | 200% | 276% | 164% | 140% | 0.522 |
| No press 130° C. H$_2$O | 120% | 152% | 100% | 88% | 0.326 |
| Room Temp. no press H$_2$O | 101% | 140% | 95% | 64% | 0.192 |

Although these spectral differences do not indicate a major change in the overall structure of the peptide, they do indicate that the samples prepared by the hot press technique contain more β-like sheet conformation than the sample prepared at 130° C. without pressure and significantly more than samples prepared at room temperature without pressure.

IX. Mass Spectrometry

The same $K_3h_9K_3$ samples used in the FTIR studies were analyzed by matrix assisted, laser desorption mass spectrometry. At elevated pH and temperature, the spontaneous hydrolysis of peptide bonds could occur. Dried samples taken from glass slides treated with 4% peptide solutions at pH 12 and dried at either room temperature or 130° C. without pressure as well as dried at 130° C. with pressure were dissolved in acetonitrile containing matrix and transferred to mass spectral target slides. Analysis of all samples revealed intact monomer however no detectable amounts of fragmented peptide observed (data not shown).

X. Introduction of Helical Structure

Figure 7:
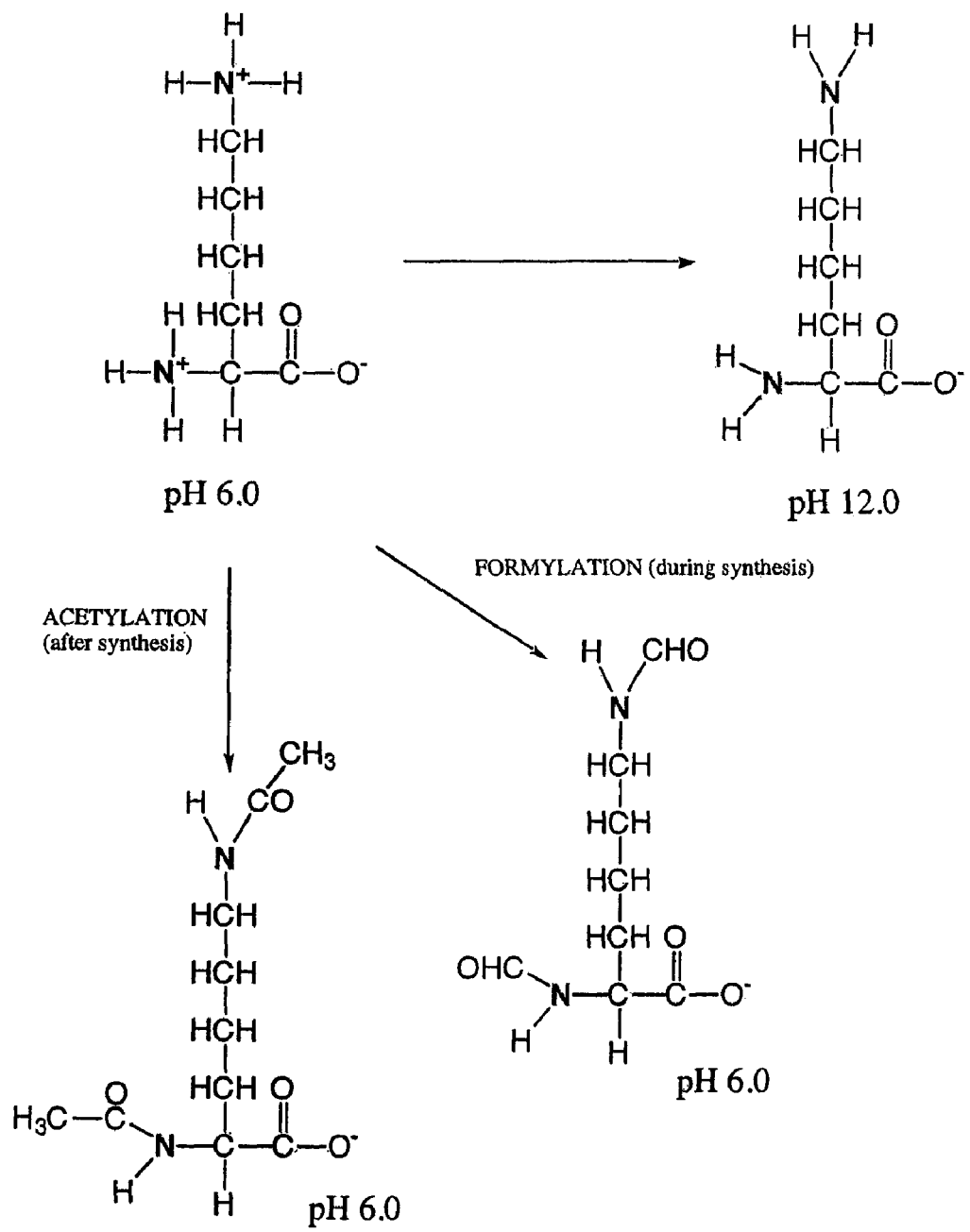
FIG. 7 presents various synthetic schemes for reducing the charge on lysine residues.

As shown in FIG. 6 the $K_3h_{5c}K_3$ sequence (KKKIGSIKKK) (SEQ ID NO: 18) has adhesive strength at pH 12.0 equal to or better than those sequences with larger hydrophobic cores (i.e. $h_7$-$h_{12}$). While the present invention is not dependent on any specific mechanism, at pH 12 the amino acid lysine looses its positive charge and becomes less water soluble (top line in FIG. 7). In loosing the positive charge, the repulsive forces are eliminated and the peptide is able to assume the beta structure. As illustrated in FIG. 7 the charge can also be eliminated by chemically modifying the $NH_2$ group by the addition of acetyl (left side reaction) or formyl (center reaction) groups. For the acetylation reaction, acetic anhydride was used to directly acetylate the fully synthesized peptide. The resulting sample, "Acylated-($K_3h_{5c}K_3$)", was separated using a RP-HPLC column on a Beckman HPLC system using the SYNERGI 4μ, 150×4.6 mm I.D. column with a mobile phase gradient starting with 95:5, water:acetonitrile containing 0.01% trifluoroacetic acid and rising to 10:90 water:acetonitrile containing 0.01% trifluoroacetic acid over 30 min at a flow rate of 1.0 ml/min with peak detection of 230 nm.

Figure 8A:
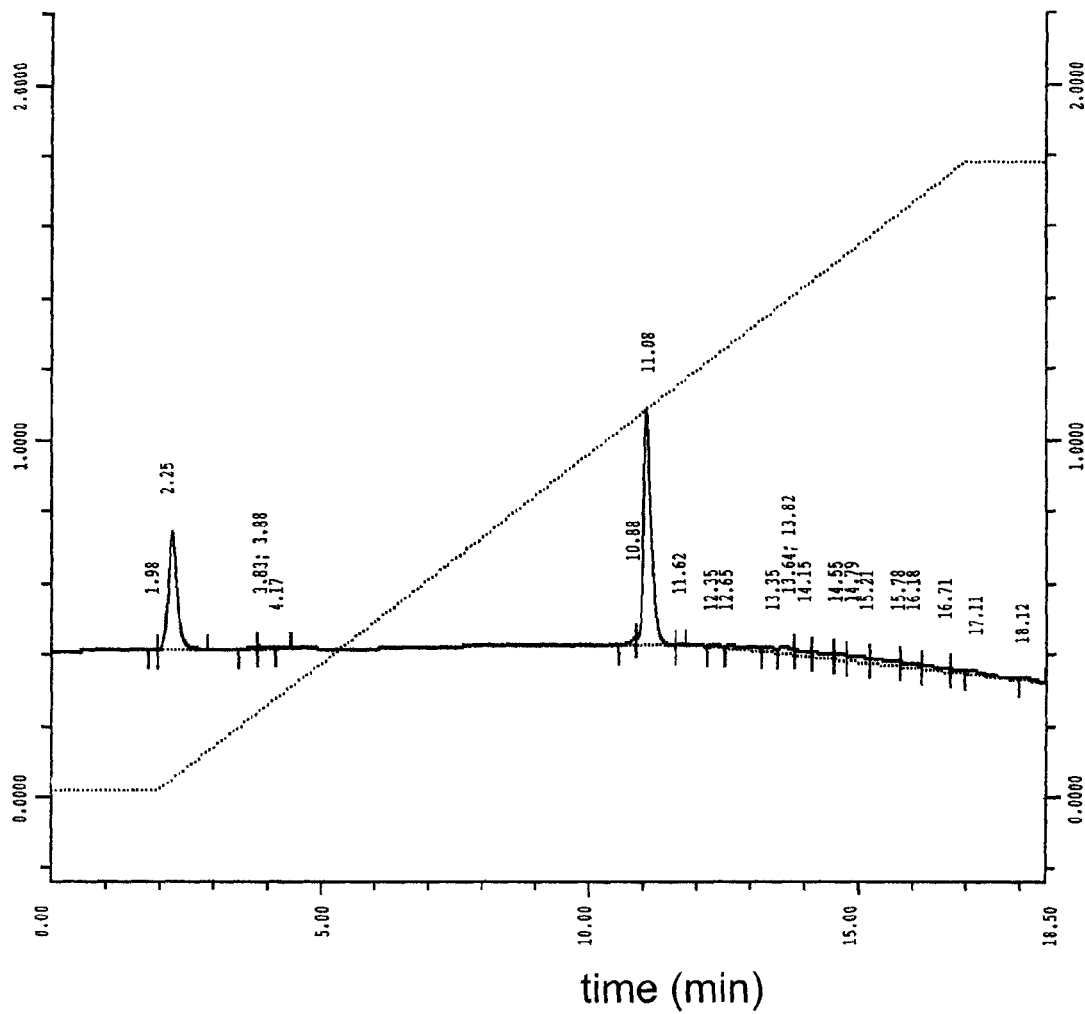
FIG. 8A is a graphic representation of the resolution of peptides after direct acetylation.
Figure 8B:
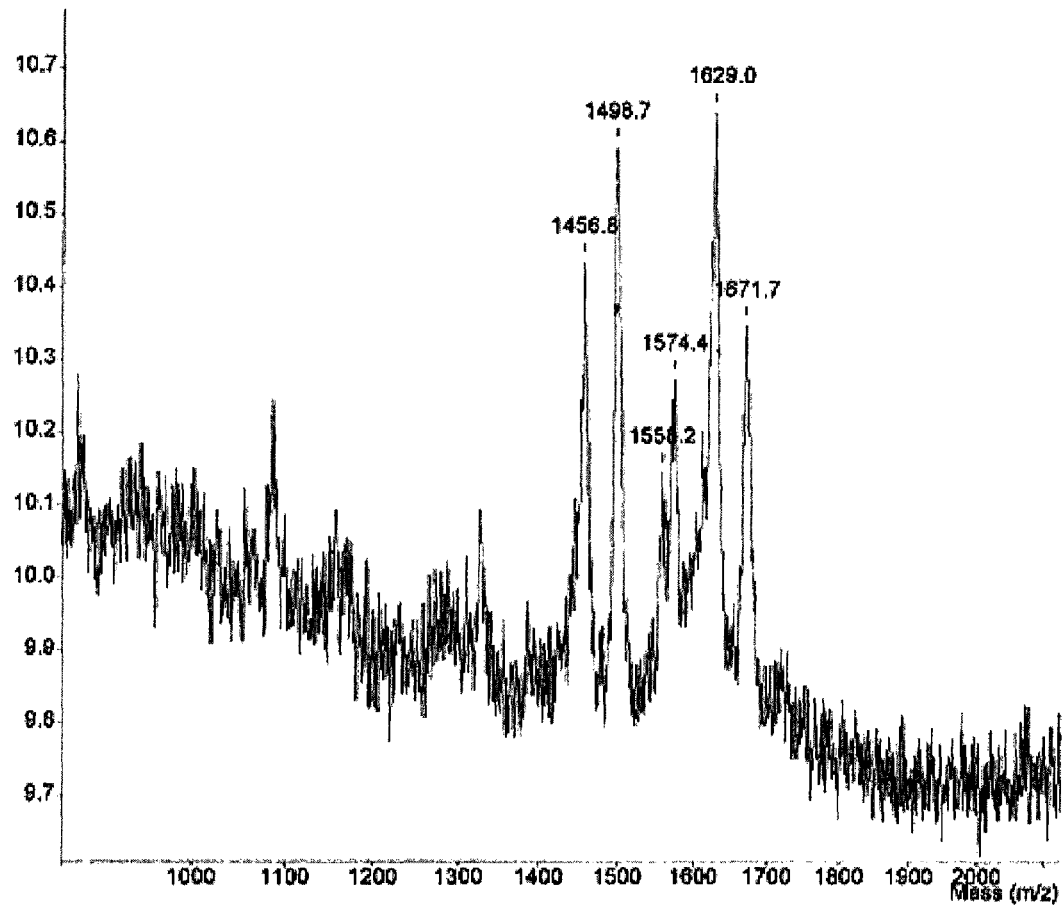
FIG. 8B is a graphic representation of the mass spectral analysis of the peptides in FIG. 8A.
Figure 9A:
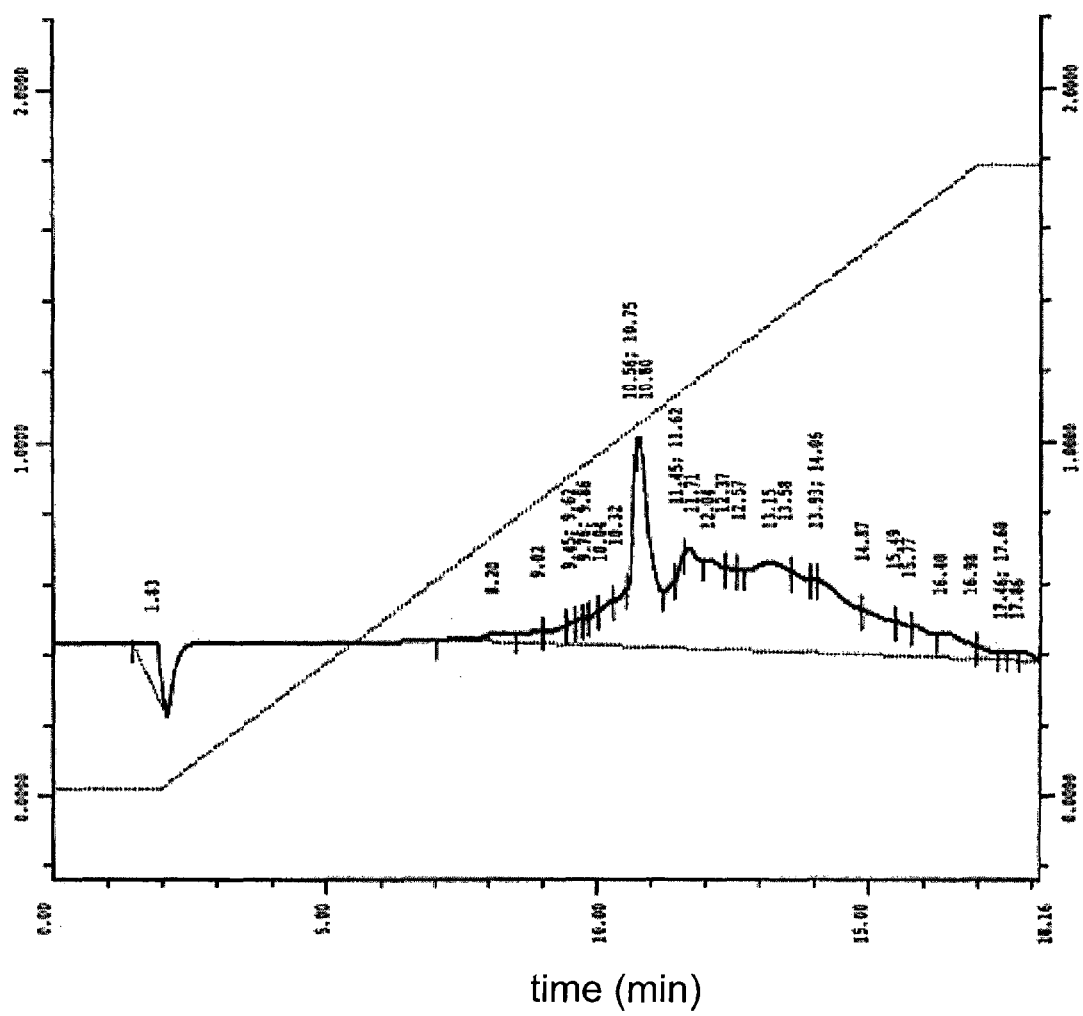
FIG. 9A is a graphic representation of the resolution of peptides resynthesized with lysine residues blocked via formylation.
Figure 9B:
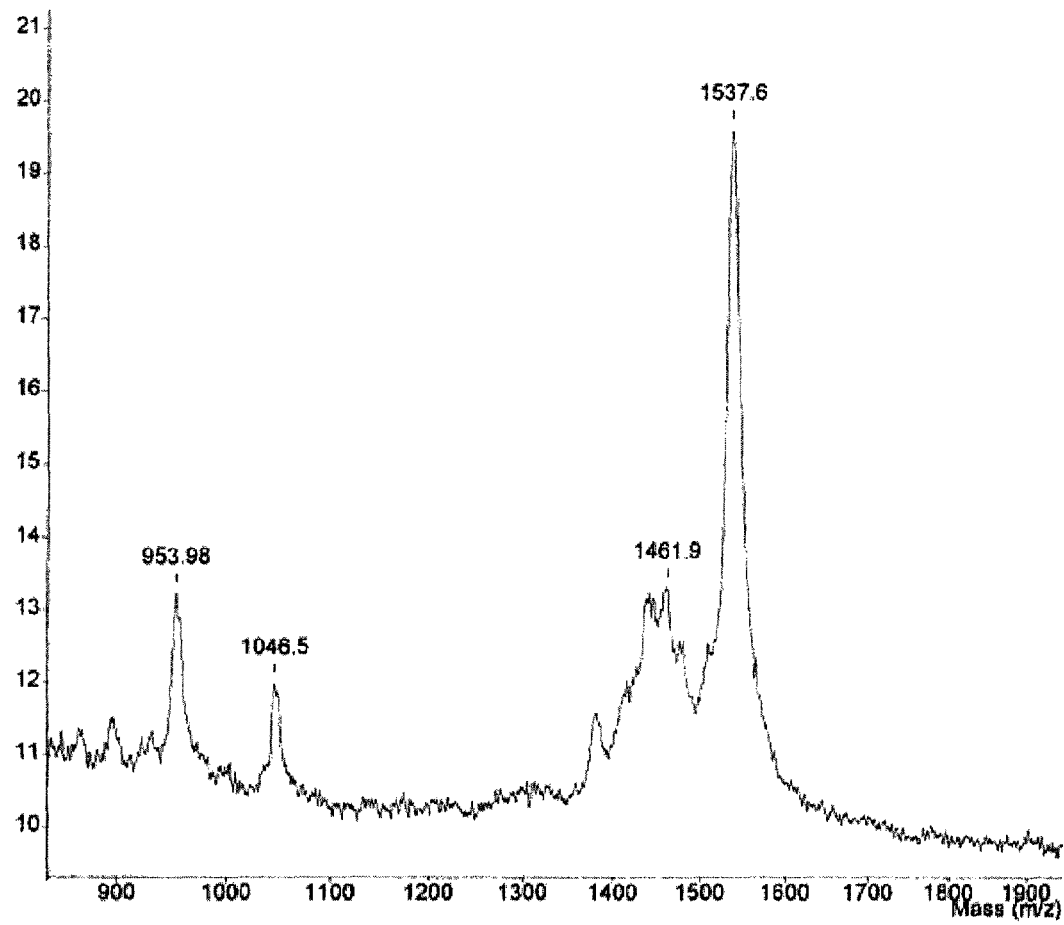
FIG. 9B is a graphic representation of the mass spectral analysis of the peptides in FIG. 9A.

As shown in FIG. 8A, the mixture of peptides derived from the direct acetylation protocol (as outlined above) were poorly separated. Subsequent analysis using MALDI-TOF mass spectrometry (see, FIG. 8B) revealed the presence of numerous products with acetylation addition numbers ranging from 4-7. In view of these results, an alternative synthetic scheme was devised. Specifically, the peptide was resynthesized with the lysine residues already blocked via formylation (see, FIG. 7). The formyl groups were added during the actual peptide synthesis using a commercially available formylated form of amino acid lysine. By adding them to the synthesis, all of the lysines were uniformly modified. The fully synthesized formylated peptide was cleaved from the resin using trifluoroacetic acid (95%) and (5%) de-ionized water; precipitated and washed several times with diethyl ether. The sample was dissolved in acetic acid and then freeze dried in a lyophilizer. The dried peptide was re dissolved in water containing 10% acetonitrile. Samples were injected into the HPLC apparatus. Maldi-TOF mass spectrometry on these samples resolved several peaks that could be assigned to the peptide sample (see, FIGS. 9A and 9B). Specifically, FIG. 9A documents one main peak in the mixture. FIG. 9B shows the anticipated mass of the product is present as well. This is the preferred synthetic method for producing an uncharged $K_3h_{5c}K_3$ molecule.

Figure 10A:
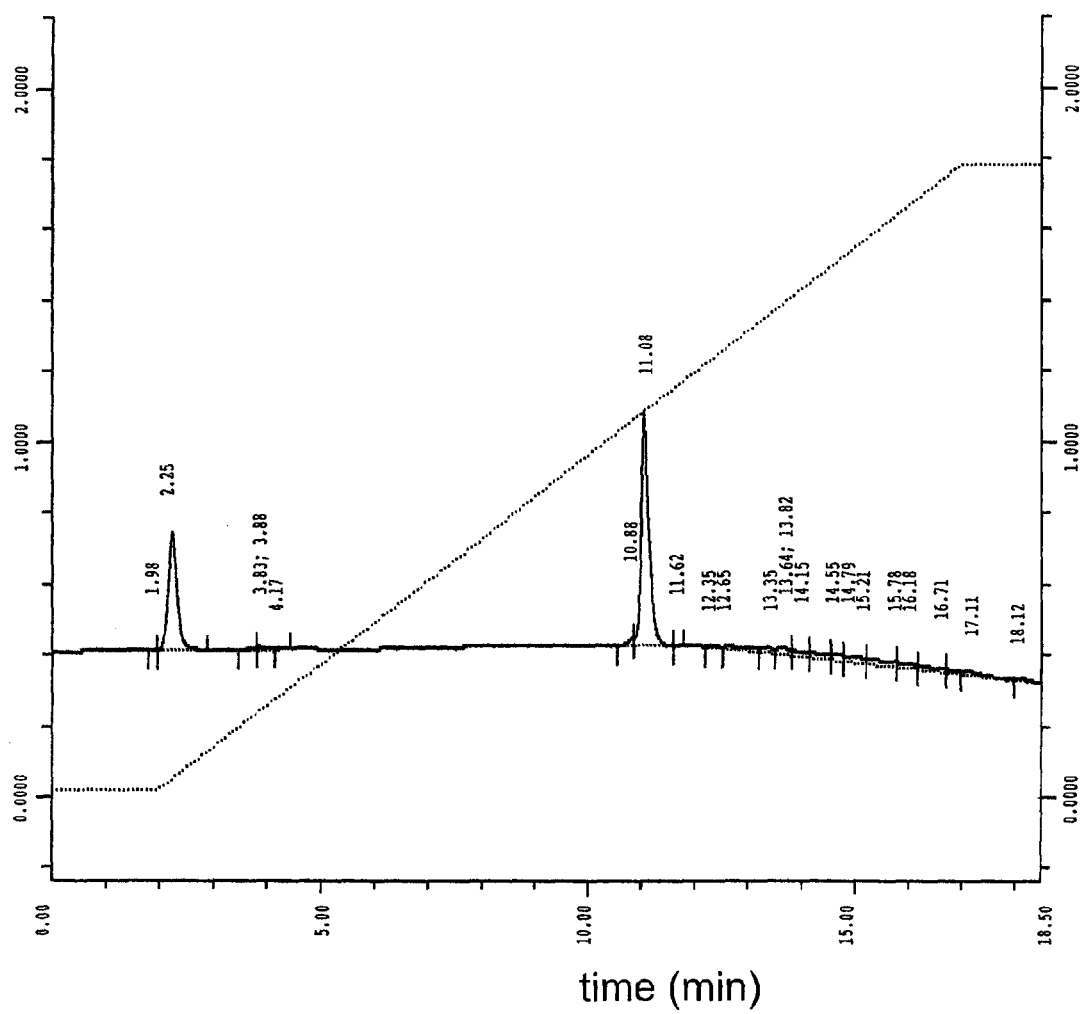
FIG. 10A is a graphic representation of the HPLC analysis of purified formylated $K_3h_5K_3$.
Figure 10B:
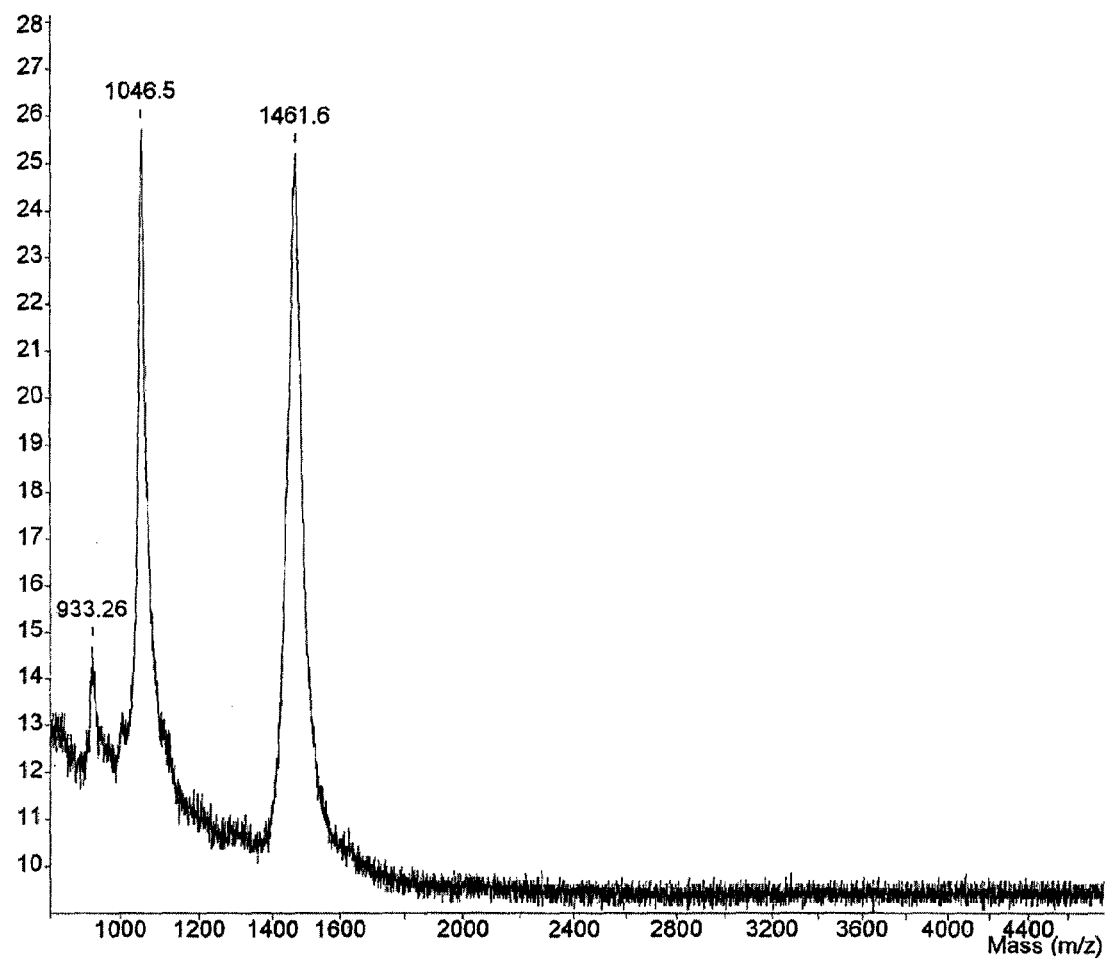
FIG. 10B is a graphic representation of the mass spectral analysis of purified formylated $K_3h_{5c}K_3$.

Having validated the isolation protocol, purified material was isolated from the crude sample by repetitive HPLC runs. Material was collected from a particular peak. Various amounts of the peptide (100 μL to 300 μL at a concentration of 0.1 mg/mL) were loaded onto the HPLC column. The purification protocol was repeated until ~10 mg of purified $K_3h_{5c}K_3$ was isolated (see FIGS. 10A and 10B). This amount was required for the structural studies that included circular dichroism (CD) and nuclear magnetic resonance (NMR).

XI Determination of the Secondary Structure

The secondary structure the $K_3h_{5c}K_3$ sequence KKKIGSIIKKK) (SEQ ID NO: 18) was measured initially in water containing the dibasic buffer salt $K_2HPO_4$ at pH 8.5. A 3mL stock sample of peptide at (1 mg/11 mL) in 5% acetonitrile in water. Peptide samples, 100 μL, were added to a quartz cuvette along with the buffer, $K_2HPO_4$, at the following concentrations: 0%, 0.01%, 0.1%, 1%, and 5%. Given that a mixture of random folding and beta sheets folding was observed, the buffer system was subsequently switched to the monobasic buffer salt, $KH_2PO_4$.

Two stock solutions of purified peptide at concentrations of 500 mM and 1 mM were prepared in water containing 5% acetonitrile at pH 4.5. The circular dichroism spectra revealed the presence of both random coil and beta-structure, with slightly more beta-structure observed in the monobasic solution. In view of this spectra the salt buffer switched in favor of distilled water at pH 5.0. This gave predominantly beta-structure (see, FIG. 11). A peptide sample (1.4 mL) containing 1.0 mM peptide—$K_3h_{5c}K_3$ sequence (KKKIGSIIKKK) (SEQ ID NO: 18)—in distilled water containing 5% acetonitrile and 10% $D_2O$ was prepared for the NMR studies. The 1D proton NMR spectrum was acquired with an 11.75 T Varian UNITY plus spectrometer (Varian, Palo Alto, Calif., USA), operating at 499.96 MHz for H, with a 3-mm triple-resonance inverse detection probe. The spectrum was recorded at 25° C. and the data processed by Varian software VNMR 6.1c on a Sun Microsystems workstation. The H NMR spectrum is shown in FIG. 12. These sharp and well separated peaks indicated the peptide did not aggregate. An analysis of the Cα protons reveal a downfield shifted as compared to unstructured protein standards. This downfield shift is consistent with a protein comprising a beta-structure conformation.

X. ΔG (Kcal/mol) Values

The following values, ΔG (Kcal/mol), were recorded for transfer from water to organic phase (a measure of hydrophobicity from Wimley and White Hydrophobicity Scale):

| Leu | −1.25 | Group "A" aliphatic and aromatic amino acids with |
| Ile | −1.12 | negative hydrophobicity values |
| Met | −0.67 | |
| Val | −0.46 | |
| Phe | −1.71 | |
| Gly | 1.15 | |
| Ser | 0.46 | Group "B" small uncharged amino acids with slightly |
| Ala | 0.50 | positive hydrophobicity values |

XI. Conclusion

The present invention contemplates a rational design approach to construct a functional peptide adhesive. In one embodiment a peptide adhesive comprises the amino acid sequence KKKFLIVIGSIIKKK ($K_3h_9K_3$) (SEQ ID NO: 7), wherein said nine sequence includes a central nine amino acid hydrophobic sequence (e.g., similar to that found in a transmembrane segment of naturally occurring ion channel proteins), and two flaming tri lysyl peptide segments that are hydrophilic and quite soluble at acidic and neutral pH values yet form hydrophobic viscose gels at pH 12. In another embodiment, the adhesive peptides are made and stored under conditions where there are no adhesive properties and then converted to the adhesive form with a simple pH change. In another embodiment, the adhesive protein comprises antiparallel beta sheets (verified using. structural analysis at elevated pH, both in solution and in a dried adhesive suggests the presence of an anti-parallel beta sheet structure.

The behavior of peptides in the absence of bulk water and treatment with higher temperatures and pressures are not well documented. Clearly in the case of this adhesive peptide, structure appears to be preserved even after subjecting the peptide to these extreme conditions. Although it is not necessary to understand the mechanism of the invention, it is believed that a peptide adhesive containing neutralized charged residues can form hydrophobic and hydrogen bonding interactions with itself and substrate surfaces as water is removed during the drying process.

In one embodiment, the adhesive comprises an aggregated β-sheet matrix stabilized further by the presence of van der Waals interactions within the hydrophobic core segment. At the two substrate surfaces, the chemical composition of the wood can form associations with the peptide adhesive and the topography (small pores and crevices) can fill with the gelling peptide such that the two surfaces become glued through the common gel matrix with both bonding and non bonding interactions.

Although it is not necessary to understand the mechanism of an invention, it is believed that, at the molecular level, there appear to be two requirements for adhesion; 1) the peptide needs to be in a β-sheet conformation where H-bonds contribute to intermolecular assembly and 2) the requirement for a substantial number of hydrophobic amino acids with suitable side chain alkyl groups capable of forming van der Waals interactions. Ionic and covalent bonds do not appear to be observed for this peptide sequence.

In another embodiment, the aforementioned nine amino acid hydrophobic core is lengthened with additional amino acid residues. In another embodiment the aforementioned nine amino acid hydrophobic core is shortened. In one embodiment beta sheet conformations were introduced into the adhesive peptides. In another embodiment the hydrophobicity of adhesive proteins was modulated. In one embodiment the flanking peptide sequences were varied.

EXPERIMENTAL

The following examples are intended as illustrative embodiments. It is not intended that these examples limit the invention in any manner. For this example, a nine residue hydrophobic sequence, FLIVIGSII ($h_9$) (SEQ ID NO: 2), was used that is derived for the third transmembrane domain of subunit IV in the dihydropyridine sensitive human muscle L-type calcium channel (IVS3) DPWNVFDFLIIGSIID-VILSE (SEQ ID NO: 14) (Grove et al., 1993). The complete 22-residue sequence is extremely hydrophobic, and once lyophilized, it aggregates to become insoluble in virtually any solvent or mixture of solvents. A strong aggregating property is a positive factor when considering a de novo design for a protein adhesive.

Next, clusters of anionic-oligo glutamate (E), cationic-oligo lysine (K), or oligo 2,3-diaminopropionate (X) residues were placed at either termini of the hydrophobic core sequence. Many protein adhesive embodiments may be contemplated, comprising different numbers and combinations of the charged residues comprising motifs including, but not limited to, $E_3h_9E_3$, $K_3h_9E_3$, $E_3h_9K_3$, $K_3h_9K_3$, $X_3h_9X_3$, $K_3h_9K_3h_9K_3$ and $K_3h_9K_3h_9K_3h_9K_3$.

Materials: Dichloromethane (DCM), dimethylformamide (DMF), ethyl ether, and N-methylpyrrolidone (NMP) were purchased from Fisher Biotech (Fair Lawn, N.J.); 1,2-ethanedithiol (EDT), N,N-diisopropylethylamine (DIEA), piperidine, and trifluoroacetric acid (TFA) were purchased from Aldrich (Milwaukee, Wis.; (2-(1H-Benzotriazol-1-yl) 1,1,3,3-tetramethyluronium hexafluorophosphate) (HBTU) and 1-hydroxybenzotriazole (HOBT) were purchased from Q-Biogene (Carlsbad, Calif.); all protected amino acids, Fmoc-Glu(tBu)-Wang resin, Fmoc-lys(Boc)-HMP, and HMP-amide resin were purchased from AnaSpec, Inc (San Jose, Calif.). CLEAR-amide resin was purchased from Peptide International (Louisville, Ky.). All reagents were ACS certified unless specified otherwise. Cherry wood samples were purchased from the Veneer One (Oceanside, N.Y.).

Peptide Synthesis: All peptides reported in Table 1 were synthesized according to the automated base-labile 9-fluorenylmethoxycarbonyl (Fmoc) strategy using Fmoc-protected amino acids, including Fmoc, Boc-2,3-diaminopropionic acid (AnaSpec, Inc, San Jose, Calif.) and Fmoc-Glu(tBu)-Wang, Fmoc-Lys(Boc)-HMP, HMP-amide resins on an Applied Biosystems Model 431 peptide synthesizer. All peptides were cleaved from the resin with simultaneous deprotected by treatment with 5% 1,2-Ethanedithiol in 95% Trifluoroacetic acid for 2 h at room temperature. The cleaved peptides were washed three-times with diethyl ether and dissolved in 20% acetonitrile in water, then lyophilized. All syntheses were characterized by matrix-assisted laser desorption time-of-flight mass spectroscopy (MALDI-TOF, MS) (FINNIGAN MAT, San Jose, Calif.). All peptide samples reported in FIG. 13 were synthesized according to the automated base-labile 9-fluorenylmethoxycarbonyl (Fmoc) strategy using Pmoc-protected amino acids CLEAR-amide resin on an Applied Biosystems Model 431 peptide synthesizer. The peptides were cleaved from the resin with simultaneous deprotection by treatment with 5% 1,2-Ethanedithiol in 95% Trifluoroacetic acid for 2 h at room temperature. The cleaved peptides were washed three-times with diethyl ether and dissolved in 20% acetonitrile in water, then lyophilized. All syntheses were characterized by matrix-assisted laser desorption ionization-time of flight-m as spectroscopy (MALDI-TOF-MS, FINNIGAN MAT, San Jose, Calif.).

Adhesive and Specimen Preparation: Adhesive stocks were prepared and stirred for 1 h, and then pH of the adhesives was adjusted using either 1N sodium hydroxide or 1N hydrochloric acid. In one embodiment, a 4% stock (w/w) was prepared such that when 360 μl of the adhesive was brushed onto each side of a wood sample, with a marked area of 8 cm×20 cm, an adhesive concentration of 0.9 mg/cm² was achieved. The wood pieces were allowed to rest at room temperature for 15 min and then were assembled and pressed by using a Hot Press (Model 3890 Auto "M"; Carver Inc., Wabash, Ind.) at pressure of 1.4 MPa at 130° C. for 5 min.

Preparation of Specimen: Wood Specimens for Shear Strength Testing were Prepared and tested according to ASTM Standard Method D2339-98. For most experiments a 4% (w/w) peptide solution was used: after stirring at room temperature for 60 min the pH was adjusted according to the pH specifications of the individual experiment. In a typical experiment a stock 20 solution of 64 mg of peptide was dissolved in 1.4 mL of water. The pH was adjusted using either 1.0 N HCl or NaOH and the final volume adjusted to 1.6 mL. Three hundred sixty milligrams of protein solution was placed on each side of a wood piece and spread on a marked area of 80 mm×20 mm. Two wood pieces were allowed to rest at room temperature for 15 min and then were assembled and press-cured using a Hot Press (Model 3890 Auto "M"; Carver Inc., Wabash, Ind.) at molding pressure of 1.4 MPa at 130° C. for 5 min. The wood specimens were preconditioned at 23° C. and 50% relative humidity (RH) for 3 days before cutting into three pieces with a glue area of 20 mm×20 mm. Then the specimens were further conditioned for 4 days before testing for shear strength.

Hydrophobicity Calculation: Hydrophobicity is represented by $\Delta G_{avg}$ in Kcal/mol. $\Delta G_{avg} = \Delta G_{residue}$/residue number. $\Delta G_{residue}$ values are taken from the Octanol—Interface Scale. Given 5 there are no published values for the hydrophobicity of lysine at pH 12.0, the value for leucine was selected.

Adhesive Strength measurement: The glued and cured wood specimens for shear strength testing were prepared according to the Standard Test Method for Strength Properties of Adhesive in Two-Ply Wood Construction in Shear by Tension Loading (ASTM D2339-98, 2002). The cherry wood specimens were preconditioned at 23° C. and 50% relative humidity (RH) for 3 days, cut into three pieces with a glue area of 20 mm×20 mm. Then the samples were further conditioned for 4 days before testing for shear strength. An Instron testing machine (Model 4465, Canton, Mass.) with a crosshead speed of 1.6 mm/min was used. Stress at maximum load was recorded and the shear strength was computed accordingly by dividing the bonded area. The shear strengths reported are the average values of at least five measurements each. Results reported were an average of six replicates. The range for the data points is included on the graphs (error bars). Wood failure was estimated according to Standard Practice for estimating the percentage of wood failure in adhesive bonded joints ASTM D5266-99 (20). The maximum load was recorded and the shear strength computed.

Water resistance: Water resistance was measured following Standard Test Methods for 25 Resistance of Adhesives to Cyclic Laboratory Aging Conditions (ASTM D1183-96, 2002) and Standard Test Methods for Effect of Moisture and Temperature on Adhesive Bonds (ASTM D1151-00, 2002). The glued wood pieces were allowed to soak in tap water at 23° C. for 48 h. The wet strength was obtained by testing immediately after soaking. The shear strength was tested as described above.

Viscosity: Viscosity of peptides at different pH was measured in a Brookfield RVDV-III 5+ viscometer (Middleboro, Mass.). All the measurements were taken at 2.5 minute intervals using 8 mL samples at ambient temperature with a spindle SC4-21 operating at 20 rpm. Five data points were averaged for each reported value.

Circular Dichroism Spectra: The data set out in FIG. 4 were collected according to the following protocol. The circular dichroic spectra were recorded on a J-720 (Jasco, Japan) spectropolarimeter with a Neslab RTE-111M circulator using a 1.0 mm quartz cuvette from 260 to 180 nm. The spectra are an average of five scans recorded at a rate of 20 nm/min with a 0.2 nm step interval. For circular dichroism measurements, 1 mL samples of synthetic peptide were prepared with a different pH buffer solution. The following buffers were used: 60 mM glycine, 60 mM NaCl, 40 mM HCl, pH 2.2; 50 mM glycine, 50 mM NaCl, 0.2 mM NaOH, pH 6.8; and 45 mM glycine, 45 mM NaCl, 55 mM NaOH, pH 12. The final peptide concentration was 250 µM. All spectra were corrected by subtracting the baseline of the buffer solution recorded under the same condition. Unless otherwise noted, spectra were recorded at room temperature. The CD absorbances were expressed as the mean residue ellipticity in units of degrees $cm^2$ $dmol^{-1}$. Temperatures were controlled with a refrigerated circulator bath (Neslab RTE-111M). Temperatures were controlled between 25° C. to 75° C.

Figure 11:
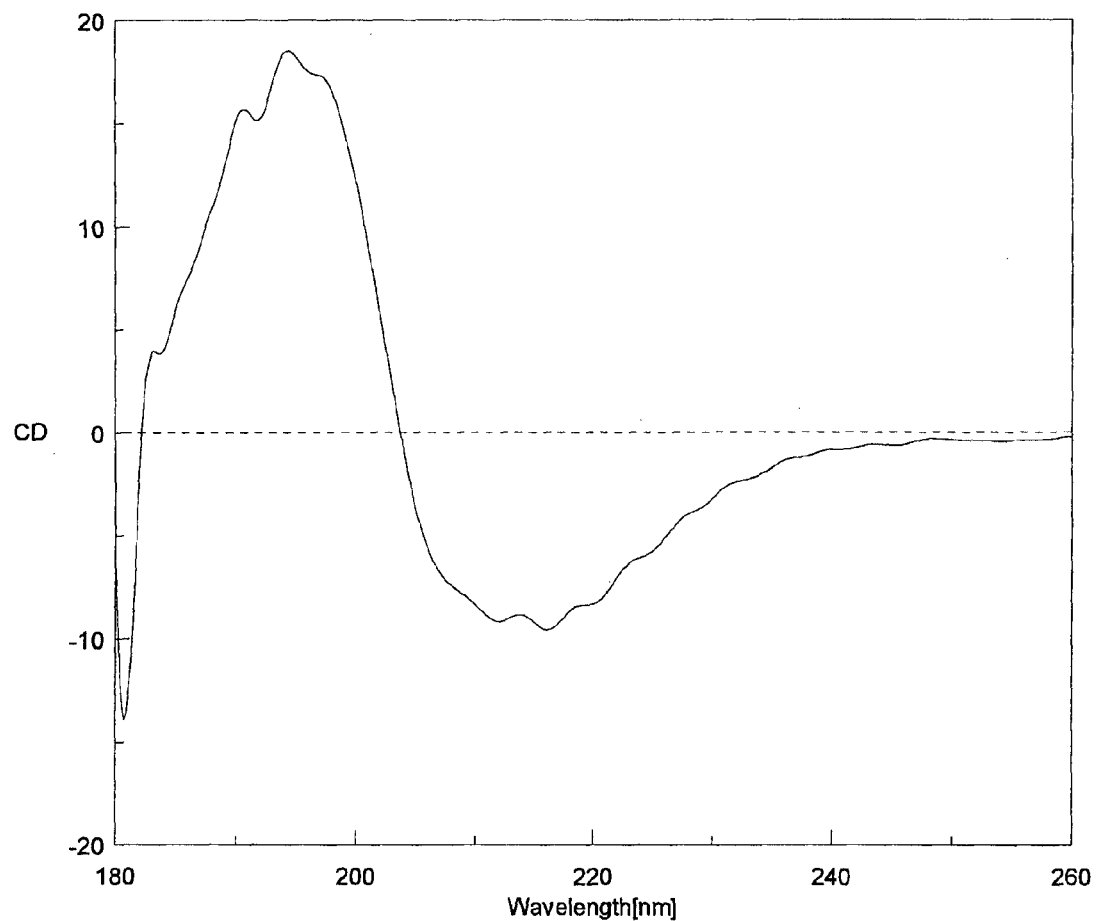
FIG. 11 projects the circular dichroism of purified formylated $K_3h_{5c}K_3$ (1.0 mM in H2O).
Figure 12:
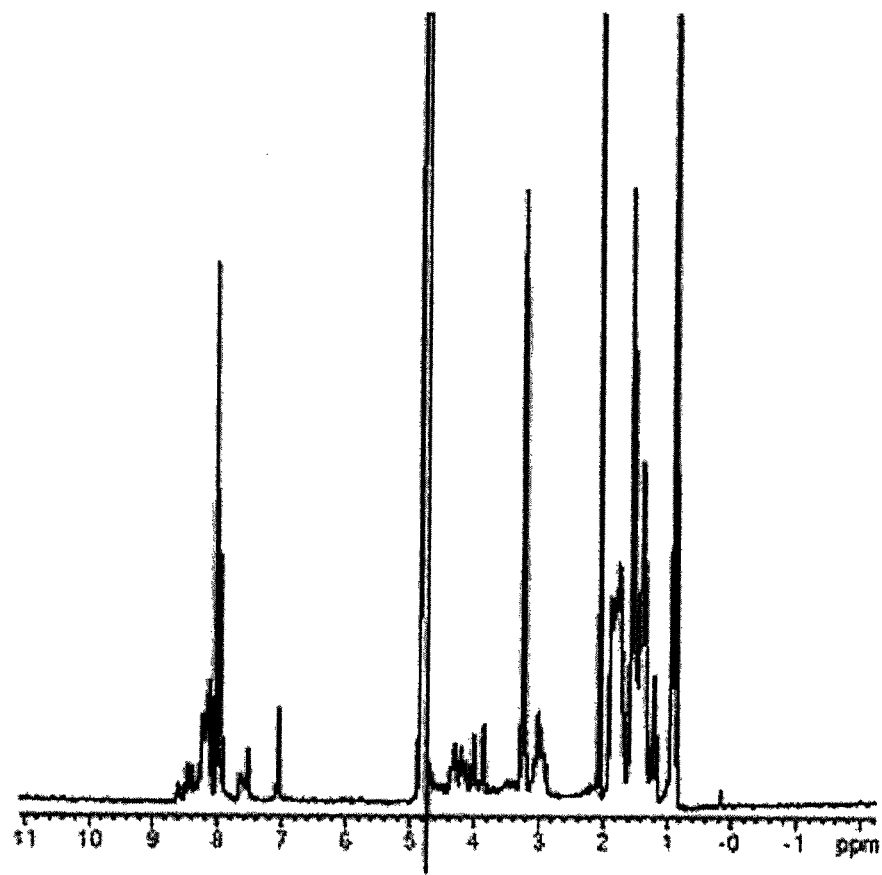
FIG. 12 projects the 1D spectrum for purified formylated $K_3h_{5c}K_3$ with 10% D2O, 5% $CH_3CN$.

The data set out in FIG. 11 were collected according to the following protocol. Circular dichroic spectra were recorded on a J-720 (Jasco, Japan) spectropolarimeter with a Neslab RTE 111M circulator using a 1.0 mm quartz cuvette from 260-180 nm. The spectra are an average of five scan recorded at a rate of 20 nm/min with a 0.2 nm step interval. For circular dichroism measurements, 1-mL samples of synthetic peptide were prepared with different solvent concentrations. The following solvent concentrations of KHPO4: 0%, 0.01%, 0.1%, 1%, and 5% in water. The final peptide concentration was 100 uM. All spectra were corrected by subtracting the baseline of the buffer solution recorded under the same condition. Unless otherwise noted, spectra were recorded at room temperature. The CD absorbances were expressed as the mean residue ellipticity in units of degree $cm^2$ dmol-1. Temperatures were controlled with a refrigerated circulator bath (Neslab RTE-111M0. Temperatures were controlled between 25 and 75 degrees Celsius. Sample spectra were recorded immediately after the instrument was purged.

Infrared Spectroscopy: A 4% $K_3h_9K_3$ peptide water solution at pH 12 was applied to the ends of glass slides, 400 mm (20×20 mm) glass slides with overall dimensions of 80×20 mm, and hot pressed as before at 130° C. Higher hot press temperatures resulted in failure of the glass. The peptide showed adhesive strength of 0.55 MPa with glass slides compared to 3.05 MPa seen glued wood strips (under identical conditions). For IR measurements, cured glass slides were pulled apart and the dried peptide film scraped off. Approximately 1 mg of dried adhesive was ground in a mortar and pestle with 10 mg predried KBr in a glove box to minimize contributions of water to the IR bands centered at around 1635-40 cm-1 that can obscure or be mistaken for the Amide I of β-sheet. The finely ground mixture was pressed to 5000-6000 lbs for 4 min in a Carver Laboratory Press Model B to produce a translucent pellet. The IR spectra were recorded on a Nicolet Nexus 670 FTIR ESP. The spectra are an average of 32 scans at 2 $cm^{-1}$ resolution. All spectra were corrected by subtracting the background. The instrument was purged every 5 min with nitrogen. Sample spectra were recorded immediately after the instrument was purged.

We claim:

1. An adhesive peptide selected from the group consisting of: $E_3h_9E_3$ (SEQ ID NO: 4), $K_3h_9E_3$ (SEQ ID NO: 5), $E_3h_9K_3$ (SEQ ID NO: 6), $K_3h_9K_3$ (SEQ ID NO: 7) and $X_3h_9X_3$ (SEQ ID NO: 10),
   wherein
   $h_9$ is the hydrophobic core sequence FLIVIGSII (SEQ ID NO: 2);
   $K_3$ is the tripeptide lysine-lysine-lysine;
   $E_3$ is the tripeptide glutamic acid-glutamic acid-glutamic acid; and
   $X_3$ is the tripeptide diaminopropionic acid-diaminopropionic acid-diaminopropionic acid.

2. An adhesive peptide selected from the group consisting of: $(K_3h_9)_2K_3$ (SEQ ID NO: 8) and $(K_3h_9)_3K_3$ (SEQ ID NO: 9),
   wherein
   $h_9$ is the hydrophobic core sequence FLIVIGSII (SEQ ID NO: 2); and
   $K_3$ is the tripeptide lysine-lysine-lysine.

3. An adhesive peptide selected from the group consisting of: SEQ ID NOs: 25-29, 31 and 32.

4. A composition comprising an adhesive peptide of claims 1, 2 or 3.

5. A method comprising:
   a) providing:
      i) a peptide selected from the group consisting of SEQ ID NOs: 4-10, 25-29, 31 and 32;
      ii) a solution having an approximate pH of 12;
   b) contacting said peptide with said solution under conditions that create an adhesive peptide.

6. A kit for the preparation of an adhesive peptide comprising: a syringe having a first barrel, said first barrel filled with an aqueous solution of a peptide selected from the group consisting of SEQ ID NOs: 4-10, 25-29, 31 and 32, buffered to maintain a pH between 6 and 7, and a second barrel, said second barrel filled with a base having a pH of approximately 12, wherein said first and second barrels are operably linked to a tip having a single lumen, wherein said lumen is in fluidic communication with said first and second barrels.

* * * * *

SEQUENCE LISTING

```
<160> NUMBER OF SEQ ID NOS: 33

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Ala Lys Pro Ser Tyr Pro Pro Thr Tyr Lys
1               5                   10

<210> SEQ ID NO 2
<211> LENGTH: 9
<212> TYPE: PRT
<213> ORGANISM: Mus musculus

<400> SEQUENCE: 2
```

```
Phe Leu Ile Val Ile Gly Ser Ile Ile
1               5

<210> SEQ ID NO 3
<211> LENGTH: 24
<212> TYPE: PRT
<213> ORGANISM: Artificial Sequence
<220> FEATURE:
<223> OTHER INFORMATION: Synthetic

<400> SEQUENCE: 3

Lys Lys Lys Phe Leu Ile Val Ile Gly Ser Ile Ile Lys Lys Lys Phe
1               5                   10                  15

Leu Ile Val Ile Gly Ser Ile Ile
            20

<210> SEQ ID NO 4
<211> LENGTH: 15
<212> TYPE: PRT
<213> ORGANISM: Artificial Sequence
<220> FEATURE:
<223> OTHER INFORMATION: Synthetic

<400> SEQUENCE: 4

Glu Glu Glu Phe Leu Ile Val Ile Gly Ser Ile Ile Glu Glu Glu
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic

<400> SEQUENCE: 5

Lys Lys Lys Phe Leu Ile Val Ile Gly Ser Ile Ile Glu Glu Glu
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Synthetic

<400> SEQUENCE: 6

Glu Glu Glu Phe Leu Ile Val Ile Gly Ser Ile Ile Lys Lys Lys
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Lys Lys Lys Phe Leu Ile Val Ile Gly Ser Ile Ile Lys Lys Lys
1               5                   10                  15

<210> SEQ ID NO 8
<211> LENGTH: 27
<212> TYPE: PRT
<213> ORGANISM: Artificial Sequence
<220> FEATURE:
<223> OTHER INFORMATION: Synthetic
```

<400> SEQUENCE: 8

Lys Lys Lys Phe Leu Ile Val Ile Gly Ser Ile Ile Lys Lys Lys Phe
1               5                   10                  15

Leu Ile Val Ile Gly Ser Ile Ile Lys Lys Lys
            20                  25

<210> SEQ ID NO 9
<211> LENGTH: 39
<212> TYPE: PRT
<213> ORGANISM: Artificial Sequence
<220> FEATURE:
<223> OTHER INFORMATION: Synthetic

<400> SEQUENCE: 9

Lys Lys Lys Phe Leu Ile Val Ile Gly Ser Ile Ile Lys Lys Lys Phe
1               5                   10                  15

Leu Ile Val Ile Gly Ser Ile Ile Lys Lys Lys Phe Leu Ile Val Ile
            20                  25                  30

Gly Ser Ile Ile Lys Lys Lys
        35

<210> SEQ ID NO 10
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: diaminopropionic acid
<220> FEATURE:
<221> NAME/KEY: MISC_FEATURE
<222> LOCATION: (13)..(15)
<223> OTHER INFORMATION: diaminopropionic acid

<400> SEQUENCE: 10

Xaa Xaa Xaa Phe Leu Ile Val Ile Gly Ser Ile Ile Xaa Xaa Xaa
1               5                   10                  15

<210> SEQ ID NO 11
<211> LENGTH: 27
<212> TYPE: PRT
<213> ORGANISM: Artificial Sequence
<220> FEATURE:
<223> OTHER INFORMATION: Synthetic

<400> SEQUENCE: 11

Lys Lys Lys Phe Leu Ile Val Ile Gly Ser Ile Ile Lys Lys Lys Phe
1               5                   10                  15

Leu Ile Val Ile Gly Ser Ile Ile Lys Lys Lys
            20                  25

<210> SEQ ID NO 12
<211> LENGTH: 15
<212> TYPE: PRT
<213> ORGANISM: Artificial Sequence
<220> FEATURE:
<223> OTHER INFORMATION: Synthetic

<400> SEQUENCE: 12

His His His Phe Leu Ile Val Ile Gly Ser Ile Ile His His His
1               5                   10                  15

```
<210> SEQ ID NO 13
<211> LENGTH: 15
<212> TYPE: PRT
<213> ORGANISM: Artificial Sequence
<220> FEATURE:
<223> OTHER INFORMATION: Synthetic

<400> SEQUENCE: 13

Arg Arg Arg Phe Leu Ile Val Ile Gly Ser Ile Ile Arg Arg Arg
1               5                   10                  15

<210> SEQ ID NO 14
<211> LENGTH: 22
<212> TYPE: PRT
<213> ORGANISM: Mus musculus

<400> SEQUENCE: 14

Asp Pro Trp Asn Val Phe Asp Phe Leu Ile Val Ile Gly Ser Ile Ile
1               5                   10                  15

Asp Val Ile Leu Ser Glu
            20

<210> SEQ ID NO 15
<211> LENGTH: 12
<212> TYPE: PRT
<213> ORGANISM: Artificial Sequence
<220> FEATURE:
<223> OTHER INFORMATION: Synthetic

<400> SEQUENCE: 15

Phe Leu Ile Val Ile Gly Ser Ile Ile Val Ile Leu
1               5                   10

<210> SEQ ID NO 16
<211> LENGTH: 5
<212> TYPE: PRT
<213> ORGANISM: Mus musculus

<400> SEQUENCE: 16

Phe Leu Ile Val Ile
1               5

<210> SEQ ID NO 17
<211> LENGTH: 5
<212> TYPE: PRT
<213> ORGANISM: Homo sapiens

<400> SEQUENCE: 17

Ile Gly Ser Ile Ile
1               5

<210> SEQ ID NO 18
<211> LENGTH: 11
<212> TYPE: PRT
<213> ORGANISM: Artificial Sequence
<220> FEATURE:
<223> OTHER INFORMATION: Synthetic

<400> SEQUENCE: 18

Lys Lys Lys Ile Gly Ser Ile Ile Lys Lys Lys
1               5                   10

<210> SEQ ID NO 19
<211> LENGTH: 14
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Residue is valine and may be present or absent
<220> FEATURE:
<221> NAME/KEY: MISC_FEATURE
<222> LOCATION: (2)..(2)
<223> OTHER INFORMATION: Residue is phenylalanine and may be present or
      absent
<220> FEATURE:
<221> NAME/KEY: MISC_FEATURE
<222> LOCATION: (12)..(12)
<223> OTHER INFORMATION: Residue is valine and may be present or absent
<220> FEATURE:
<221> NAME/KEY: MISC_FEATURE
<222> LOCATION: (13)..(13)
<223> OTHER INFORMATION: Residue is isoleucine and may be present or
      absent
<220> FEATURE:
<221> NAME/KEY: MISC_FEATURE
<222> LOCATION: (14)..(14)
<223> OTHER INFORMATION: Residue is leucine and may be present or absent

<400> SEQUENCE: 19

Xaa Xaa Phe Leu Ile Val Ile Gly Ser Ile Ile Xaa Xaa Xaa
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic

<400> SEQUENCE: 20

Lys Lys Lys Ala Ala Ala Ala Ala Lys Lys Lys
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Synthetic

<400> SEQUENCE: 21

Lys Lys Lys Ala Ala Ala Ala Ala Asx Asx Ala Ala Lys Lys Lys
1               5                   10                  15

<210> SEQ ID NO 22
<211> LENGTH: 11
<212> TYPE: PRT
<213> ORGANISM: Artificial Sequence
<220> FEATURE:
<223> OTHER INFORMATION: Synthetic

<400> SEQUENCE: 22

Lys Lys Lys Ala Asx Asx Ala Ala Lys Lys Lys
1               5                   10

<210> SEQ ID NO 23
<211> LENGTH: 4
<212> TYPE: PRT
<213> ORGANISM: Artificial Sequence
<220> FEATURE:
<223> OTHER INFORMATION: Synthetic

<400> SEQUENCE: 23
```

```
Phe Leu Ile Val
1

<210> SEQ ID NO 24
<211> LENGTH: 4
<212> TYPE: PRT
<213> ORGANISM: Artificial Sequence
<220> FEATURE:
<223> OTHER INFORMATION: Synthetic

<400> SEQUENCE: 24

Gly Ser Ile Ile
1

<210> SEQ ID NO 25
<211> LENGTH: 11
<212> TYPE: PRT
<213> ORGANISM: Artificial Sequence
<220> FEATURE:
<223> OTHER INFORMATION: Synthetic

<400> SEQUENCE: 25

Lys Lys Lys Ile Gly Ser Ile Ile Lys Lys Lys
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic

<400> SEQUENCE: 26

Lys Lys Lys Phe Leu Ile Val Ile Lys Lys Lys
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Lys Lys Ile Gly Ser Ile Ile Lys Lys
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Lys Lys Phe Leu Ile Val Ile Lys Lys
1               5

<210> SEQ ID NO 29
<211> LENGTH: 13
<212> TYPE: PRT
<213> ORGANISM: Artificial Sequence
<220> FEATURE:
<223> OTHER INFORMATION: Synthetic

<400> SEQUENCE: 29

Lys Lys Lys Phe Leu Ile Val Ile Gly Ser Lys Lys Lys
```

-continued

```
<210> SEQ ID NO 30
<211> LENGTH: 15
<212> TYPE: PRT
<213> ORGANISM: Artificial Sequence
<220> FEATURE:
<223> OTHER INFORMATION: Synthetic

<400> SEQUENCE: 30

Lys Lys Lys Phe Leu Ile Val Ile Gly Ser Ile Ile Lys Lys Lys
1               5                   10                  15

<210> SEQ ID NO 31
<211> LENGTH: 17
<212> TYPE: PRT
<213> ORGANISM: Artificial Sequence
<220> FEATURE:
<223> OTHER INFORMATION: Synthetic

<400> SEQUENCE: 31

Lys Lys Lys Val Phe Phe Leu Ile Val Ile Gly Ser Ile Ile Lys Lys
1               5                   10                  15

Lys

<210> SEQ ID NO 32
<211> LENGTH: 18
<212> TYPE: PRT
<213> ORGANISM: Artificial Sequence
<220> FEATURE:
<223> OTHER INFORMATION: Synthetic

<400> SEQUENCE: 32

Lys Lys Lys Phe Leu Ile Val Ile Gly Ser Ile Ile Val Ile Leu Lys
1               5                   10                  15

Lys Lys

<210> SEQ ID NO 33
<211> LENGTH: 16
<212> TYPE: PRT
<213> ORGANISM: Artificial Sequence
<220> FEATURE:
<223> OTHER INFORMATION: Synthetic

<400> SEQUENCE: 33

Lys Ala Lys Ala Lys Ala Lys Ala Glu Ala Glu Ala Glu Ala Glu Ala
1               5                   10                  15
```